US009821165B2

(12) United States Patent
Gross

(10) Patent No.: US 9,821,165 B2
(45) Date of Patent: *Nov. 21, 2017

(54) METHOD FOR SYMMETRY-BASED IMPLANT CONTROL

(71) Applicant: BLUEWIND MEDICAL LTD., Herzlia (IL)

(72) Inventor: Yossi Gross, Moshav Mazor (IL)

(73) Assignee: BLUEWIND MEDICAL LTD., Herzlia (IL)

(*) Notice: Subject to any disclaimer, the term of this patent is extended or adjusted under 35 U.S.C. 154(b) by 0 days.

This patent is subject to a terminal disclaimer.

(21) Appl. No.: 15/270,434

(22) Filed: Sep. 20, 2016

(65) Prior Publication Data

US 2017/0007829 A1   Jan. 12, 2017

Related U.S. Application Data

(63) Continuation of application No. 14/445,443, filed on Jul. 29, 2014, now Pat. No. 9,457,186.
(Continued)

(51) Int. Cl.
*A61N 1/05*   (2006.01)
*A61N 1/36*   (2006.01)
(Continued)

(52) U.S. Cl.
CPC .......... *A61N 1/3611* (2013.01); *A61B 5/0488* (2013.01); *A61B 5/076* (2013.01);
(Continued)

(58) Field of Classification Search
CPC ............ A61N 1/05; A61N 1/36; A61N 1/372; A61N 1/3601; A61N 1/3611;
(Continued)

(56) References Cited

U.S. PATENT DOCUMENTS 6,587,725 B1 * 7/2003 Durand ................ A61N 1/3601
607/118
7,054,692 B1   5/2006 Whitehurst et al.
(Continued)

OTHER PUBLICATIONS

An Office Action dated Feb. 27, 2017, which issued during the prosecution of U.S. Appl. No. 14/649,873.
(Continued)

*Primary Examiner* — Carl H Layno
*Assistant Examiner* — Jon Eric C Morales
(74) *Attorney, Agent, or Firm* — Sughrue Mion, PLLC

(57) ABSTRACT

Apparatus comprising (1) a breathing sensor, configured to detect a breathing-related factor of a subject; (2) at least a first electrode configured to be placed in a vicinity of a respective first hypoglossal nerve, and to be driven, in response to the detected breathing-related factor, to apply a first electrical current to the first hypoglossal nerve; (3) at least a second electrode configured to be placed in a vicinity of a respective second hypoglossal nerve, and to be driven, in response to the detected breathing-related factor, to apply a second electrical current to the second hypoglossal nerve; and (4) circuitry configured to, in response to a detected symmetry-related factor indicative of a degree of symmetry of the subject, configure at least one current selected from the group consisting of: the first current and the second current. Other embodiments are also described.

25 Claims, 13 Drawing Sheets

Related U.S. Application Data

(60) Provisional application No. 61/860,323, filed on Jul. 31, 2013.

(51) Int. Cl.
| | | |
|---|---|---|
| *A61N 1/375* | (2006.01) | |
| *A61N 1/378* | (2006.01) | |
| *A61B 5/08* | (2006.01) | |
| *A61N 1/372* | (2006.01) | |
| *A61B 5/0488* | (2006.01) | |
| *A61B 5/07* | (2006.01) | |
| *A61B 5/00* | (2006.01) | |
| *A61B 5/113* | (2006.01) | |

(52) U.S. Cl.
CPC .............. *A61B 5/08* (2013.01); *A61B 5/4818* (2013.01); *A61B 5/4836* (2013.01); *A61N 1/0548* (2013.01); *A61N 1/36139* (2013.01); *A61N 1/36157* (2013.01); *A61N 1/36171* (2013.01); *A61N 1/3756* (2013.01); *A61N 1/3787* (2013.01); *A61N 1/37205* (2013.01); *A61B 5/0031* (2013.01); *A61B 5/113* (2013.01)

(58) Field of Classification Search
CPC .............. A61N 1/36139; A61N 1/1756; A61N 1/37205; A61B 5/08; A61B 5/076; A61B 5/4818
USPC ................................... 607/42, 116, 118, 120
See application file for complete search history.

(56) References Cited

U.S. PATENT DOCUMENTS

| | | | |
|---|---|---|---|
| 9,457,186 B2 * | 10/2016 | Gross | ................... A61N 1/3756 |
| 2002/0183805 A1 | 12/2002 | Fang et al. | |
| 2002/0183817 A1 | 12/2002 | Van Venrooij et al. | |
| 2003/0114905 A1 | 6/2003 | Kuzma | |
| 2004/0249431 A1 | 12/2004 | Ransbury et al. | |
| 2005/0113894 A1 | 5/2005 | Zilberman et al. | |
| 2005/0131495 A1 | 6/2005 | Parramon et al. | |
| 2006/0085039 A1 | 4/2006 | Hastings et al. | |
| 2007/0208392 A1 | 9/2007 | Kuschner et al. | |
| 2007/0255369 A1 | 11/2007 | Bonde et al. | |
| 2007/0255379 A1 * | 11/2007 | Williams | .......... A61M 5/14276 607/120 |
| 2007/0293912 A1 | 12/2007 | Cowan et al. | |
| 2008/0009914 A1 | 1/2008 | Buysman et al. | |
| 2010/0016911 A1 | 1/2010 | Willis et al. | |
| 2011/0251660 A1 | 10/2011 | Griswold | |
| 2013/0325081 A1 | 12/2013 | Karst et al. | |
| 2014/0135868 A1 * | 5/2014 | Bashyam | ........... A61N 1/3601 607/42 |
| 2015/0004709 A1 | 1/2015 | Nazarpoor | |
| 2017/0119435 A1 | 5/2017 | Gross et al. | |

OTHER PUBLICATIONS

An Office Action dated Apr. 5, 2017, which issued during the prosecution of U.S. Appl. No. 14/374,375.

An Office Action dated Apr. 4, 2017, which issued during the prosecution of U.S. Appl. No. 14/601,604.

An Office Action dated Dec. 12, 2016, which issued during the prosecution of U.S. Appl. No. 14/939,418.

An Office Action dated Nov. 21, 2016, which issued during the prosecution of U.S. Appl. No. 14/601,626.

* cited by examiner

METHOD FOR SYMMETRY-BASED IMPLANT CONTROL

CROSS-REFERENCES TO RELATED APPLICATIONS

This application is a Continuation of U.S. patent application Ser. No. 14/445,443 to Gross, filed Jul. 29, 2014, and entitled "Bilateral Feedback," which published as US 2015/0039046 (now U.S. Pat. No. 9,457,186), and which claims priority from U.S. Provisional Patent Application 61/860,323 to Gross, filed Jul. 31, 2013, entitled "Bilateral Feedback", which is incorporated herein by reference. This application is related to U.S. Ser. No.13/885,360 to Gross (now abandoned), which published as US 2013/0261693, and is a US national phase of PCT IL2011/000870, filed Nov. 10, 2011 and published as WO 2012/066532 to Gross, which claims the priority of, and is a continuation-in-part of, U.S. patent application Ser. No. 12/946,246, filed Nov. 15, 2010 and published as US 2012/0123498 to Gross, now abandoned, all of which are incorporated herein by reference.

FIELD OF THE INVENTION

Some applications of the present invention generally relate to medical apparatus. More specifically, some applications of the present invention relate to neurostimulator implants, and to apparatus and techniques for use therewith.

BACKGROUND

Sleep apnea is a chronic sleep breathing disorder typically characterized by abnormal pauses (apneas) in an individual's breathing, ranging from seconds to minutes in duration, or by instances of abnormally low breathing. Sleep apnea is associated with cardiovascular disease, myocardial infarction, high blood pressure, stroke, arrhythmias, diabetes, sleep-deprived driving accidents, and cerebrovascular disease.

Current treatments include positive airway pressure (PAP) therapy (e.g., continuous positive expiratory pressure; CPAP), oral appliances, surgery (e.g., genioglossus advancement, tongue radiofrequency treatment, midline glossectomy, hyoid suspension and maxillomandibular advancement), lifestyle changes (e.g., positional therapy and weight loss), and implantable muscle stimulators.

SUMMARY OF THE INVENTION

For some applications of the invention, two implants are implanted in a vicinity of respective hypoglossal nerves of a subject, each implant comprising at least one electrode. A breathing sensor is configured to detect a breathing-related factor of a subject. A driver is configured to drive each electrode to apply a respective electrical current to a respective hypoglossal nerve. Circuitry is configured to calibrate the currents applied by the electrodes in response to a detected symmetry-related factor that is indicative of a degree of symmetry of the subject. For some such applications, a symmetry sensor detects the symmetry-related factor.

For some applications the symmetry sensor is extracorporeal. For some applications the symmetry sensor is implantable. For some applications the breathing sensor is intracorporeal. For some applications the breathing sensor is implantable.

There is therefore provided, in accordance with an application of the present invention, apparatus for use with a body of a subject, the apparatus including:

a breathing sensor, configured to detect a breathing-related factor of the subject;

at least a first electrode configured to be placed in a vicinity of a respective first hypoglossal nerve of the subject, and to be driven, in response to the detected breathing-related factor, to apply a first electrical current to the first hypoglossal nerve;

at least a second electrode configured to be placed in a vicinity of a respective second hypoglossal nerve of the subject, and to be driven, in response to the detected breathing-related factor, to apply a second electrical current to the second hypoglossal nerve; and circuitry configured to, in response to a detected symmetry-related factor indicative of a degree of symmetry of the subject, configure at least one current selected from the group consisting of: the first current and the second current.

In an application, the breathing sensor includes exactly one breathing sensor.

In an application, the first electrode and the second electrode are configured to be placed by being injected into the subject.

In an application, the circuitry is further configured to configure at least the first electrical current to initiate action potentials in the first hypoglossal nerve without directly initiating contraction of muscle of the subject.

In an application, the circuitry is further configured to configure at least the first electrical current to have a frequency of between 10 and 40 Hz.

In an application, the circuitry is further configured to configure at least the first electrical current to have an amplitude of between 0.1 and 3 mA.

In an application, the apparatus further includes at least one driver, configured to drive at least one electrode selected from the group consisting of: the at least first electrode and the at least second electrode.

In an application, the at least one driver includes exactly one driver, configured to wirelessly drive the at least first electrode and the at least second electrode.

In an application, the at least one driver includes (1) a first driver, coupled to the at least first electrode, and configured to drive the at least first electrode, and (2) a second driver, coupled to the at least second electrode, and configured to drive the at least second electrode.

In an application, the apparatus further includes a symmetry sensor, configured to detect the symmetry-related factor.

In an application, the symmetry sensor is configured to detect a mechanical symmetry of the subject.

In an application, the symmetry sensor includes an accelerometer.

In an application, the symmetry sensor is configured to detect an electrical symmetry of the subject.

In an application, the symmetry sensor includes an electrode.

In an application, the electrode includes an electromyographic electrode.

In an application, the apparatus further includes an extracorporeal control unit that includes the symmetry sensor, and is configured to transmit a wireless signal at least in part responsively to the detected symmetry-related factor.

In an application, the extracorporeal control unit further includes the breathing sensor.

In an application, the circuitry is configured to receive the wireless signal, and to configure the at least one selected current in response to receiving the wireless signal.

In an application, the extracorporeal control unit is configured to provide power wirelessly to the circuitry.

In an application, the circuitry includes a first circuitry configured to configure the first current in response to the detected symmetry-related factor, and the apparatus further includes:

a first implant, configured to be implanted in the vicinity of the first hypoglossal nerve, and including the first electrode and the first circuitry; and a second implant, configured to be implanted in the vicinity of the second hypoglossal nerve, and including the second electrode and second circuitry configured to configure the second current in response to the detected symmetry-related factor.

In an application, the apparatus further includes a control unit, including a symmetry sensor, configured to detect the symmetry-related factor, to transmit a wireless signal at least in part responsively to the detected symmetry-related factor, and to configure the wireless signal to independently address the first implant and the second implant.

In an application, at least one implant selected from the group consisting of: the first implant and the second implant, includes the breathing sensor.

In an application, at least one implant selected from the group consisting of: the first implant and the second implant, includes a symmetry sensor, configured to detect the symmetry-related factor.

In an application, the apparatus further includes a control unit, including the circuitry, and configured to configure at least the at least one selected current in response to the detected symmetry-related factor.

In an application, the control unit includes an implantable control unit implantable in the body of the subject.

In an application, the control unit includes the breathing sensor.

In an application, the control unit includes exactly one control unit, and is configured to configure the first current and the second current in response to the detected symmetry-related factor.

In an application, the control unit includes an extracorporeal control unit.

In an application, the control unit includes a symmetry sensor, configured to detect the symmetry-related factor.

In an application, the control unit is configured to configure at least the at least one selected current by transmitting a wireless signal in response to detecting the symmetry-related factor.

There is further provided, in accordance with an application of the present invention, a method for use with a body of a subject, the method including:

detecting a breathing-related factor of the subject;

in response to the detected breathing-related factor:

applying a first electrical current to a first hypoglossal nerve of the subject, and applying a second electrical current to a second hypoglossal nerve of the subject; and in response to a detected symmetry-related factor indicative of a degree of symmetry of the subject, configuring at least one current selected from the group consisting of: the first current and the second current.

In an application, the method further includes configuring at least the first electrical current to initiate action potentials in the first hypoglossal nerve without directly initiating contraction of muscle of the subject.

In an application, detecting the breathing-related factor includes extracorporeally detecting the breathing-related factor.

In an application, the method further includes detecting the symmetry-related factor.

In an application, detecting the symmetry-related factor includes detecting a mechanical symmetry of the subject.

In an application, detecting the symmetry-related factor includes detecting an electrical symmetry of the subject.

In an application, detecting the symmetry-related factor includes detecting an electromyographic factor of the subject.

In an application, detecting the symmetry-related factor includes extracorporeally detecting the symmetry-related factor.

In an application, the method further includes transmitting a wireless signal at least in part responsively to the detected symmetry-related factor.

In an application, the method further includes intracorporeally receiving the wireless signal, and configuring the at least one selected current in response to receiving the wireless signal.

In an application, the method further includes extracorporeally transmitting wireless power, and intracorporeally receiving the wireless power.

In an application, configuring the at least one selected current includes configuring the first current and the second current.

In an application, the method further includes transmitting a wireless signal at least in part responsively to the detected symmetry-related factor, and configuring the wireless signal to (1) induce the configuring of the first current, and (2) induce the configuring of the second current independently of the inducing of the configuring of the first current.

In an application:

detecting the breathing-related parameter includes detecting the breathing-related parameter using a breathing sensor;

applying the first electrical current includes applying the first electrical current using a first electrode disposed in a vicinity of the first hypoglossal nerve;

applying the second electrical current includes applying the second electrical current using a second electrode disposed in a vicinity of the second hypoglossal nerve; and configuring the at least one selected current includes configuring the at least one selected current using circuitry configured to configure the at least one selected current in response to the detected symmetry-related factor.

In an application, applying the first electrical current includes applying the first electrical current using a first electrode that has been injected into the subject.

In an application, the method further includes detecting the symmetry-related factor using a symmetry sensor.

In an application, detecting the symmetry-related factor includes detecting a mechanical symmetry of the subject.

In an application, detecting the symmetry-related factor includes detecting the symmetry-related factor using a symmetry sensor that includes an accelerometer.

In an application, detecting the symmetry-related factor includes detecting an electrical symmetry of the subject.

In an application, detecting the symmetry-related factor includes detecting the symmetry-related factor using a symmetry sensor that includes an electrode.

In an application, detecting the symmetry-related factor includes detecting the symmetry-related factor using a symmetry sensor that includes an electromyographic electrode.

In an application:

detecting the symmetry-related factor includes detecting the symmetry-related factor using an extracorporeal control unit that includes the symmetry sensor, and the method further includes transmitting a wireless signal at least in part responsively to the detected symmetry-related factor.

In an application, detecting the breathing-related factor includes detecting the breathing-related factor using the extracorporeal control unit, the extracorporeal control unit including the breathing sensor.

In an application, the method further includes receiving the wireless signal using the circuitry.

In an application, the method further includes providing power wirelessly to the circuitry using the extracorporeal control unit.

In an application:

the circuitry includes a first circuitry, a first implant includes the first circuitry and the first electrode, applying the first current includes applying the first current using the first electrode of the first implant, a second implant includes the second electrode and second circuitry, and applying the second current includes applying the second current using the second electrode of the second implant, and In an application, configuring the at least one selected current includes:

configuring the first current using the first circuitry of the first implant, and configuring the second current using the second circuitry of the second implant.

In an application, the method further includes:

detecting the symmetry-related factor using a symmetry sensor of a control unit, and using the control unit, transmitting a wireless signal at least in part responsively to the detected symmetry-related factor, and configuring the wireless signal to independently address the first implant and the second implant.

In an application, at least one implant selected from the group consisting of: the first implant and the second implant, includes the breathing sensor, and detecting the breathing-related factor includes detecting the breathing-related factor using the breathing sensor of the at least one selected implant.

In an application, at least one implant selected from the group consisting of: the first implant and the second implant, includes a symmetry sensor, and the method further includes detecting the symmetry-related factor using the symmetry sensor of the at least one selected implant.

In an application, the circuitry includes circuitry of a control unit, and configuring the at least one selected current includes configuring the at least one selected current using the circuitry of the control unit.

In an application, configuring the at least one selected current includes configuring the at least one selected current using circuitry of an implantable control unit, disposed within the body of the subject.

In an application, the control unit includes the breathing sensor, and detecting the breathing-related factor includes detecting the breathing-related factor using the breathing sensor of the control unit.

In an application, configuring the at least one selected current includes configuring the at least one selected current using circuitry of an extracorporeal control unit.

In an application, the control unit includes a symmetry sensor, and the method further includes detecting the symmetry-related factor using the symmetry sensor of the control unit.

In an application, the method further includes transmitting a wireless signal using the control unit, in response to detecting the symmetry-related factor.

In an application, the method further includes, using the circuitry, configuring at least the first electrical current to initiate action potentials in the first hypoglossal nerve without directly initiating contraction of muscle of the subject.

There is further provided, in accordance with an application of the present invention, a method, including:

implanting, in a vicinity of a first anatomical site of a subject, a first implant including at least one electrode and circuitry configured to drive the at least one electrode of the first implant to apply a first electrical current to the first anatomical site;

implanting, in a vicinity of a second anatomical site of a subject, a second implant including at least one electrode and circuitry configured to drive the at least one electrode of the second implant to apply a second electrical current to the second anatomical site; and subsequently, detecting a symmetry-related factor of the subject indicative of a symmetry of the subject, and in response to the detected symmetry-related factor, configuring at least one implant selected from the group consisting of: the first implant and the second implant.

In an application, implanting includes injecting.

In an application, implanting the first implant includes implanting the first implant in a vicinity of a first hypoglossal nerve of the subject, and implanting the second implant includes implanting the second implant in a vicinity of a second hypoglossal nerve of the subject.

In an application, detecting includes detecting a mechanical symmetry of the subject.

In an application, detecting includes detecting an electrical symmetry of the subject.

In an application, configuring includes modifying the current applied by the at least one selected implant.

In an application, modifying includes altering a balance of amplitude between the first electrical current and the second electrical current.

The present invention will be more fully understood from the following detailed description of applications thereof, taken together with the drawings, in which:

DETAILED DESCRIPTION OF EMBODIMENTS

Figure 1:
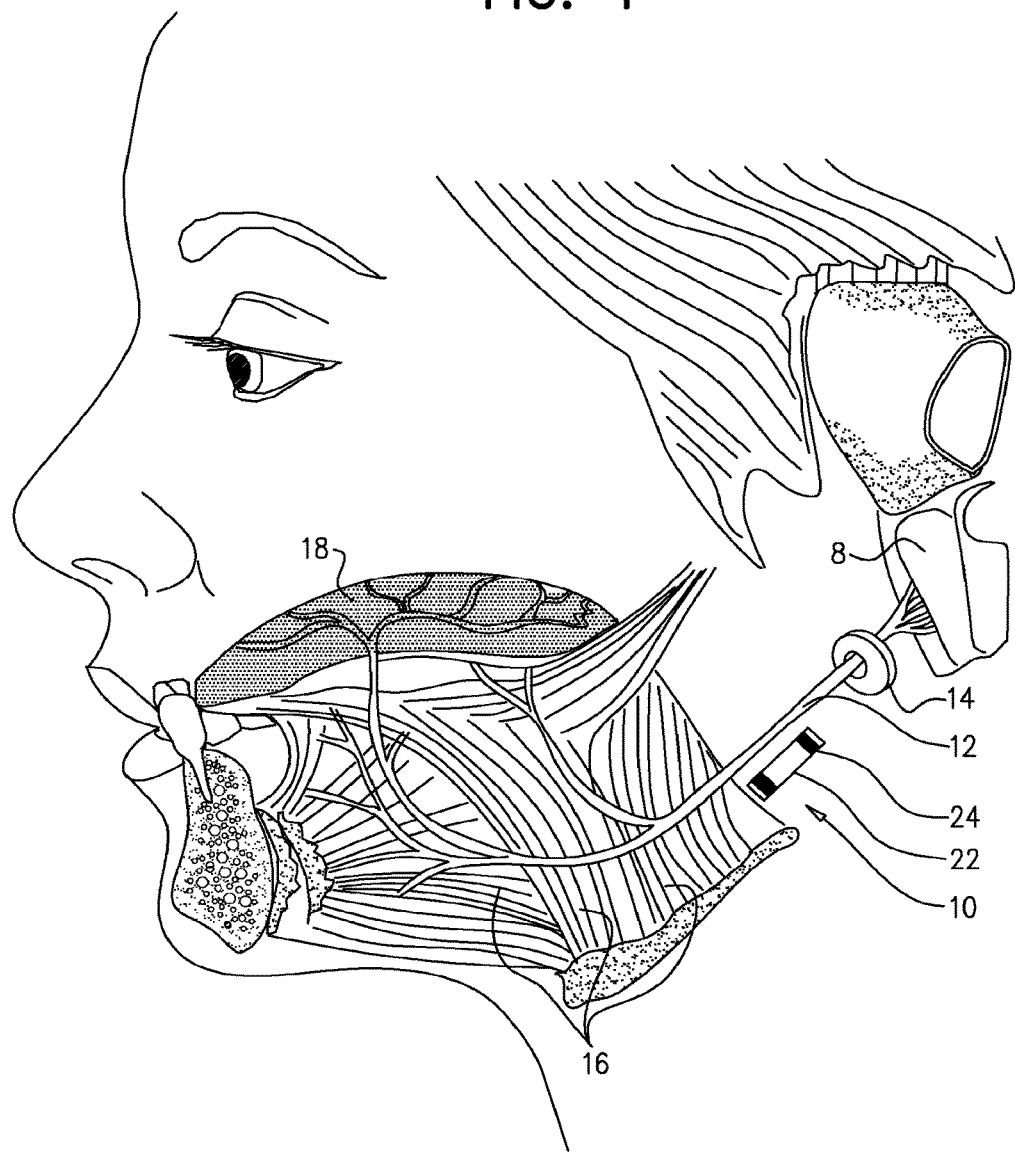
FIG. 1 is a schematic illustration of a neurostimulator implant and an implantation site therefor, in accordance with some applications of the invention.

Reference is made to FIG. 1, which is a schematic illustration of a neurostimulator implant 22 and an implantation site therefor, in accordance with some applications of the invention. Implant 22 is implanted, e.g., by being injected, at an implantation site 10 in a vicinity of a nerve of the subject, such as a hypoglossal nerve 12 of the subject.

Implant 22 comprises one or more (e.g., two) electrodes 24, and typically at least one antenna, as described hereinbelow in accordance with respective applications of the invention.

Typically, implant 22 is implanted within 8 mm (e.g., within 5 mm, e.g., within 3 mm, e.g., within 1 mm) of hypoglossal nerve 12. Further typically, implant 22 is implanted such that an electrode 24 that serves as a cathode is disposed within 5 mm (e.g., within 3 mm, e.g., within 1 mm) of the hypoglossal nerve, and/or such that an electrode 24 that serves as an anode is disposed within 8 mm (e.g., within 5 mm, e.g., within 3 mm, e.g., within 1 mm) of the hypoglossal nerve. Implant 22 may be implanted such that at least a portion of the implant (e.g., at least one electrode thereof) is in contact with the hypoglossal nerve.

For illustrative purposes, the following anatomical features are also labeled in FIG. 1: Hypoglossal canal 14, extrinsic muscles 16 of the tongue, intrinsic muscles 18 of the tongue, and medulla oblongata 8.

Implant 22 is configured to initiate action potentials in hypoglossal nerve 12 by applying an excitatory current via electrodes 24. These action potentials induce contraction of muscle tissue of the tongue. An appropriately timed application of the excitatory current during a sleep apnea event repositions the tongue, thereby interrupting the event and restoring breathing.

It is typically desirable that induced contraction of the tongue muscle tissue be generally symmetric (e.g., with respect to the central sagittal plane of the subject). Therefore, two implants 22 are typically implanted contralaterally; each implant in a vicinity of a respective hypoglossal nerve. For some applications, the symmetry of the contraction of the tongue muscle tissue is achieved and/or increased by calibrating the excitatory currents of the implants so as to provide that the excitatory current reaching each hypoglossal nerve is generally the same as the excitatory current reaching the other hypoglossal nerve (that is, generally symmetric application of excitatory current). For some applications, symmetric contraction of the tongue muscle tissue is achieved and/or increased by calibrating the excitatory currents of the implants so as to apply a different current to each hypoglossal nerve (that is, asymmetric application of excitatory current), such as in cases in which one hypoglossal nerve is less responsive to the excitatory current than is the other hypoglossal nerve.

For some applications (e.g., when the neurostimulator implant comprises an injectable implant), it may be difficult to implant the implant at a precise position and/or distance from the hypoglossal nerve, and the distance between one implant and its respective hypoglossal nerve may be different from that between the other implant and its respective hypoglossal nerve. Therefore, for some applications, it is desirable to calibrate the currents of the implants such that each implant applies a different excitatory current, e.g., to counter the difference in distance, and thereby resistance, between each implant and its respective hypoglossal nerve. Such calibration may be useful both for applications in which generally symmetric application of excitatory current is desired, and for applications in which asymmetric application of excitatory current is desired.

Therefore, calibration of the excitatory currents may comprise, with respect to one or more characteristics (e.g., amplitude and/or frequency) (1) maintaining equality between the current applied by one implant and the current applied by the other implant, or (2) creating and/or maintaining an imbalance between the current applied by one implant and the current applied by the other implant.

Typically, it is desirable to induce contraction of the muscle tissue by exciting (i.e., inducing action potentials in) the nerve, rather than by direct electrical stimulation of the muscle tissue by the implant. This is typically achieved by applying a current having a lower amplitude and a higher frequency than that used for directly stimulating muscle tissue. For example, the excitatory current may have a frequency of greater than 10 Hz, less than 40 Hz, and/or between 10 and 40 Hz, and/or may have an amplitude of greater than 0.1 mA, less than 3 mA, and/or between 0.1 and 3 mA. For such applications, the calibration of excitatory currents described hereinabove may be particularly useful e.g., such that a minimum amplitude required for a given implanted implant to excite the nerve may be established, and used by that implant, rather than that implant using a higher amplitude than that required.

It is to be noted that the hypoglossal nerve is used herein as an example, and that applications of the invention may be used to facilitate symmetric contraction of other muscles and/or excitation of other nerve pairs.

Reference is made to FIGS. 2-13, which are schematic illustrations of respective systems, each of the systems comprising two neurostimulator implants, and being configured to induce generally symmetric contraction of the tongue of the subject by calibrating respective excitatory currents applied by the neurostimulator implants, in accordance with some applications of the invention. Each of the systems described with reference to FIGS. 2-13 comprises a breathing sensor, configured to detect a breathing-related parameter of the subject, and circuitry configured to configure the current applied by at least one of the neurostimulator implants in response to a detected symmetry-related factor indicative of a symmetry of the subject. Typically, the neurostimulator implants described with reference to FIGS. 2-13 comprise, or are identical or analogous to, implants 22 described with reference to FIG. 1. Some of the systems further comprise a symmetry sensor, configured to detect the symmetry-related factor. Each system is configured such that the implants apply excitatory current in response to the breathing-related parameter, e.g., when the breathing detector detects a sleep apnea event.

Figure 2:
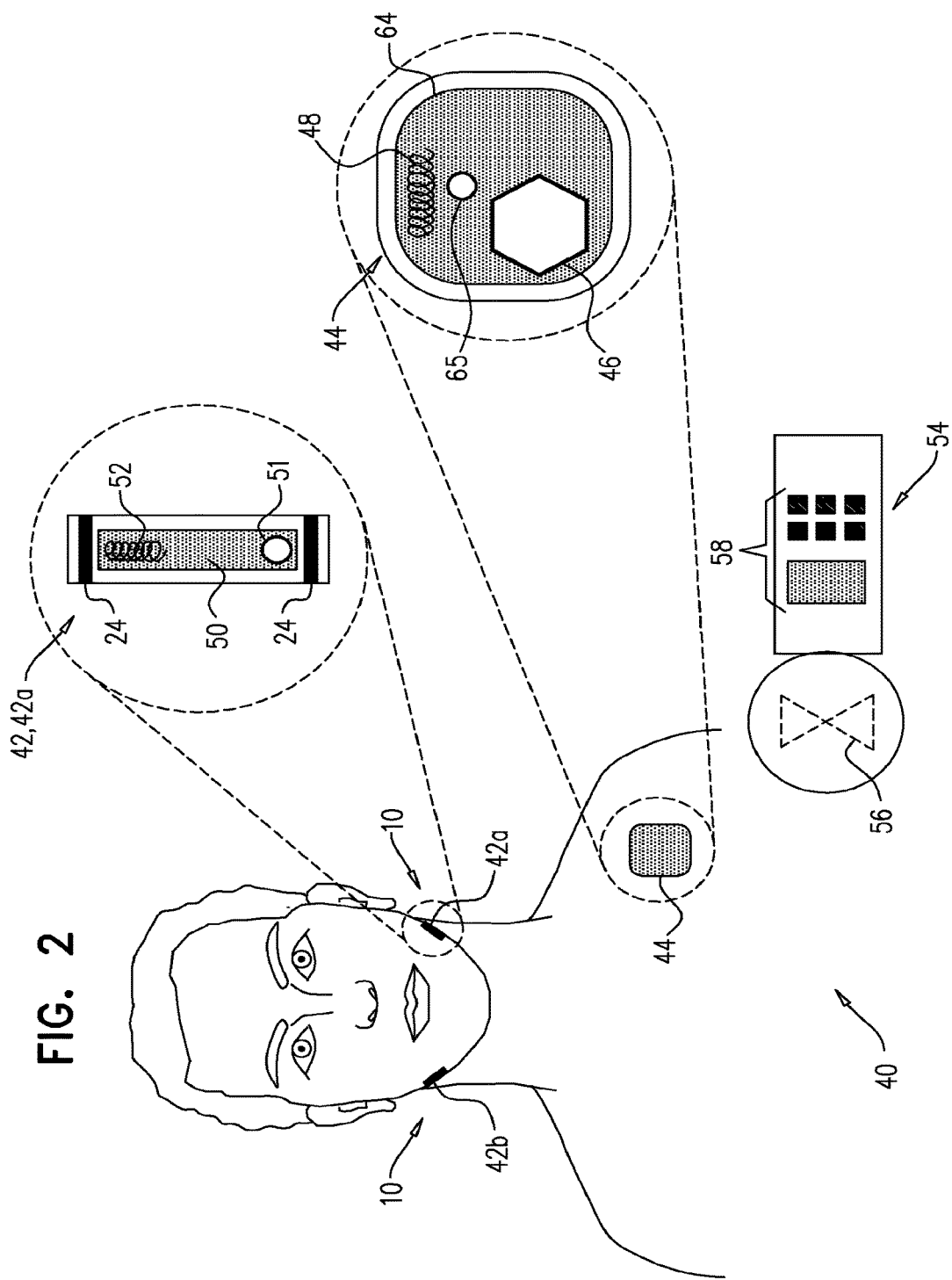
FIGS. 2-13 are schematic illustrations of respective systems, each system comprising two neurostimulator implants, and being configured to induce generally symmetric contraction of the tongue of the subject by calibrating respective excitatory currents applied by the neurostimulator implants, in accordance with some applications of the invention.

Reference is made to FIG. 2, which is a schematic illustration of a system 40, comprising two neurostimulator implants 42 (e.g., a first neurostimulator implant 42a and a second neurostimulator implant 42b), and an implantable (e.g., subcutaneously implantable) control unit 44 that comprises circuitry 64 comprising a breathing sensor 46, in accordance with some applications of the invention. Implantable control unit 44 (e.g., circuitry 64 thereof) typically comprises an antenna 48 and is configured to drive the antenna to transmit at least one wireless signal when breathing sensor 46 detects a sleep apnea event.

For some applications, breathing sensor 46 detects acceleration, momentum and/or velocity of the sensor and/or a portion of the body of the subject, caused by the breathing of the subject. Alternatively or additionally, sensor 46 may detect one or more other breathing-related factors. Sensor 46 may comprise a piezoelectric sensor, a piezoresistive sensor, a capacitive sensor, an inductive sensor, a magnetic sensor, and/or a sensor that detects variations in impedance of a conductive fluid.

For some applications, apparatus and methods described in U.S. Pat. No. 5,304,208 to Inguaggiato et al. and U.S. Pat. No. 5,454,838 to Vallana et al., which are incorporated herein by reference, are utilized in combination with the apparatus and methods described herein, in order to detect the breathing-related factor of the subject. Alternatively or additionally, sensor 46 comprises the hemodynamic sensor embedded in the tip of the SonRtip™ atrial sensing/pacing lead, which is instead positioned in the subject to directly measure pressure changes associated with respiration, rather than to measure hemodynamic parameters.

Each implant 42 comprises one or more (e.g., two) electrodes 24, and circuitry 50 comprising an antenna 52. Circuitry 50 is configured to receive (e.g., via antenna 52) the wireless signal from control unit 44, and at least in part responsively to the wireless signal, to drive the electrodes to apply the excitatory current to the hypoglossal nerve. For example, implant 42 (e.g., circuitry 50 thereof) may comprise a driver 51, configured to drive electrodes 24. Each implant 42 is independently addressable by control unit 44, e.g., by the wireless signal from the control unit being encoded. This allows control unit 44 to drive each implant to apply current that is different in one or more characteristics from current driven by the other implant, and thereby to calibrate the excitatory currents of the implants, e.g., as described hereinbelow. Typically, control unit 44 drives both implants 42 at generally the same time (e.g., simultaneously, or within 1 second of each other).

Typically, implants 42 are powered by control unit 44 via the wireless signal. That is, typically the wireless signal includes wireless power, and control unit 44 thus wirelessly drives circuitry 50 of implants 42 to drive electrodes 24 to apply the excitatory current. For example, antenna 52 may comprise an induction antenna (e.g., an induction loop) or a rectifying antenna, and control unit 44 (e.g., circuitry 64 thereof) may comprise a driver 65, configured to drive electrodes 24 via the wireless power.

System 40 further comprises an extracorporeal control unit 54, configured to configure (e.g., wirelessly) implantable control unit 44 (e.g., circuitry 64 thereof). For example, control unit 54 may comprise an antenna that communicates with antenna 48 of control unit 44. Control unit is typically configured to be used to calibrate the excitatory currents applied by implants 42, by configuring control unit 44 (e.g., circuitry 64 thereof) to calibrate the excitatory currents (e.g., to configure at least one of the currents). For example, control unit 54 may be used to configure control unit 44 to drive implant 42a to apply a current that has a first amplitude, and to drive implant 42b to apply a current that has a second amplitude that is different from (e.g., greater than) the first amplitude. This configuring is typically performed so as to increase symmetry of contraction of the tongue of the subject. Other characteristics of the excitatory current that may be modified in this way include duty cycle, and for some applications, frequency.

Subsequent to implantation of implants 42 and control unit 44 (e.g., immediately subsequently, or during a subsequent appointment), a physician detects a degree of symmetry of contraction of the tongue and/or other tissues, induced by implants 42. For some applications, the physician (1) induces control unit 44 to drive the implants as though breathing sensor 46 had detected a sleep apnea event, and (2) observes the subject visually and/or using a symmetry sensor configured to detect a symmetry-related factor (e.g., degree of symmetry) of the subject. For example, the physician may wirelessly induce control unit 44 to drive the implants, by pressing a "stimulate" button of user interface 58. In response to detecting the symmetry, control unit 44 (e.g., circuitry 64 thereof) is configured to calibrate the excitatory currents of implants 42, typically to increase the degree of symmetry. For example, if the tongue of the subject moves toward one side during contraction, control unit 54 may be used to configure control unit 44 to increase the amplitude of the current of one of implants 42 and/or reduce the amplitude of the current applied by the other implant. For example, for applications in which the characteristic of the current to be modified is amplitude, if the tongue of the subject is disposed to the right, the amplitude of the current applied by the implant on the left side of the subject may be (further) increased relative to that applied by the implant on the right side of the subject (e.g., by configuring the left-side implant to increase its current's amplitude, and/or by configuring the right-side implant to decrease its current's amplitude). As described hereinabove, other characteristics of the excitatory current that may be modified in this way include duty cycle, and for some applications, frequency. Typically, the process of calibrating the excitatory currents to increase symmetry is an iterative process.

For some applications, extracorporeal control unit 54 comprises symmetry sensor 56 (hence the symmetry sensor is shown in phantom in FIG. 2). For some applications, symmetry sensor 56 is distinct from, but can electronically interface with, control unit 54. For some applications in which control unit 54 comprises or interfaces with symmetry sensor 56, system 40 at least in part automatically performs the process of (1) inducing control unit 44 to drive the implants, (2) detecting a symmetry-related factor (e.g., a degree of symmetry), and (3) configuring control unit 44 to increase the degree of symmetry. Control unit 54 is shown in FIG. 2 as a wand-type control unit (e.g., similar in appearance to that in the pacemaker art) purely as an illustrative example, and not by way of limitation.

For some applications, symmetry sensor 56 is distinct from control unit 54 and the operating physician fully-manually or partially-manually controls control unit 54 (e.g., via a user interface 58), at least in part responsively to information received from the symmetry sensor. Interface 58 may also be used for applications in which the physician visually observes the degree of symmetry (e.g., when no symmetry sensor is used).

For some applications, symmetry sensor 56 comprises a camera, configured to detect mechanical symmetry, e.g., in combination with visual markers (e.g., fiducial markers) coupled to the subject. For some applications, symmetry sensor 56 comprises one or more induction coils, and is used to detect mechanical symmetry, e.g., in combination with magnetic markers (which may comprise, or be comprised by, implants 42), coupled to the subject. For some applications, symmetry sensor 56 comprises at least one electrode, and is configured to detect an electrical symmetry of the subject. For example, symmetry sensor 56 may be configured to detect action potentials in the hypoglossal nerve (e.g., sensor 56 may comprise an action potential sensor), or may comprise an electromyographic electrode, and be configured to detect electromyographic signals (e.g., sensor 56 may comprise an EMG sensor).

For some applications, extracorporeal control unit 54 is alternatively or additionally configured to configure implants 42 (e.g., circuitry 50 thereof) so as to calibrate excitatory currents thereof. For example, control unit 54 may be configured to configure implants 42 directly, rather than configuring implantable control unit 44. For such applications, control unit 44 may drive implants 42 (via the wireless signal) to apply the excitatory currents, but itself not calibrate the implants.

Figure 3:
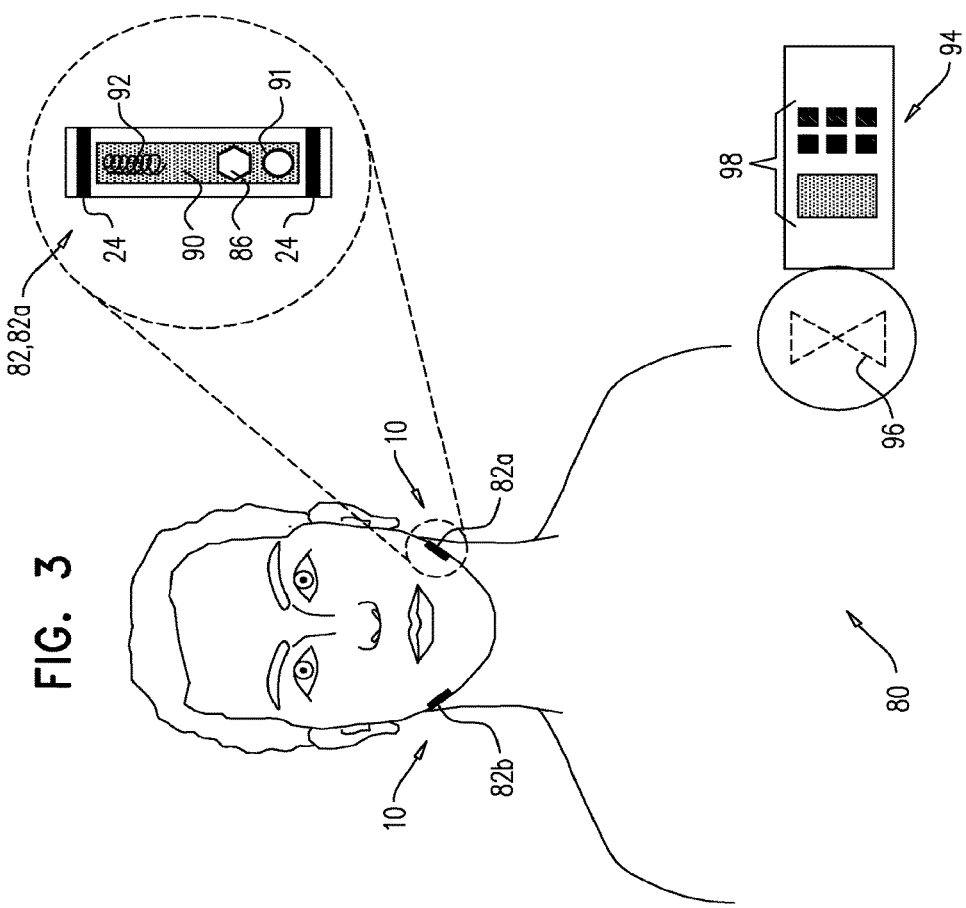

Reference is made to FIG. 3, which is a schematic illustration of a system 80, comprising two neurostimulator implants 82 (e.g., a first neurostimulator implant 82a and a second neurostimulator implant 82b), in accordance with some applications of the invention. Implants 82 are typically identical to implants 42 described hereinabove, mutatis mutandis, except for where noted. At least one of implants 82 (e.g., implant 82a, as shown) comprises a breathing sensor 86. For some applications, breathing sensor 86 may comprise breathing sensor 46 (described with reference to FIG. 2), one or more components, and/or a functionality thereof.

Implants 82 comprise electrodes 24 and circuitry 90 comprising a driver 91 configured to drive the electrodes to apply the excitatory current to the hypoglossal nerve in response to breathing sensor 86 detecting a sleep apnea event. For some applications, each of implants 82 comprises a respective breathing sensor 86, and is configured to apply the excitatory current in response to detection of the sleep apnea event by its respective breathing sensor. For some applications, at least one of implants 82 is configured to apply the excitatory current at least in part responsively to detection of the sleep apnea event by the breathing sensor of the other implant. For example, only one of implants 82 may comprise a breathing sensor 86, and both implants apply the excitatory current in response to the detection of the sleep apnea event by the one breathing sensor. For example, the implant that comprises the breathing sensor may be configured to transmit at least one wireless signal via an antenna 92 when the breathing sensor detects a sleep apnea event, and the other implant may be configured to apply the excitatory current at least in part responsively to the wireless signal.

Alternatively or additionally, both of implants 82 comprise a respective breathing sensor 86, and are configured to apply the excitatory current in response to the detection of the sleep apnea event by one or more of the breathing sensors (e.g., the implants are configured to wirelessly communicate (e.g., negotiate) via respective antennas 92 in order to collectively detect the sleep apnea event and/or to collectively determine if/when to apply the excitatory current).

It is to be noted that, in contrast to system 40 described hereinabove with reference to FIG. 2, system 80 typically does not comprise an implantable control unit that is distinct from the neurostimulator implants. That is, compared to system 40, breathing sensor functionality is moved from the distinct implantable control unit 44 to one or both of implants 82.

System 80 further comprises an extracorporeal control unit 94, configured to calibrate the excitatory currents of implants 82 by configuring (e.g., wirelessly) one or more of the implants (e.g., circuitry 90 thereof). For example, control unit 94 may be used to configure implant 82a to apply a current that has a first amplitude, and to configure implant 82b to apply a current that has a second amplitude that is different from (e.g., higher than) the first amplitude. This configuring is typically performed so as to increase symmetry of contraction of the tongue of the subject, and is typically similar to that described hereinabove for system 40, mutatis mutandis.

Subsequent to implantation of implants 82 (e.g., immediately subsequently, or during a subsequent appointment), a physician detects a degree of symmetry of contraction of the tongue and/or other tissues induced by implants 82. For some applications, the physician (1) induces implants 92 to apply the excitatory current as though breathing sensor(s) 86 had detected a sleep apnea event, and (2) observes the subject visually and/or using a symmetry sensor 96. In response to detecting the symmetry, at least one of implants 82 is configured (e.g., adjusted), typically to increase the degree of symmetry, thereby calibrating the excitatory currents of system 80. For example, if the tongue of the subject moves toward one side during contraction, control unit 94 may be used to increase the amplitude of the current of one of implants 82 and/or reduce the amplitude of the current applied by the other implant (e.g., as described hereinabove, mutatis mutandis). Typically, the process of calibrating the excitatory currents to increase symmetry is an iterative process.

For some applications, extracorporeal control unit 94 comprises symmetry sensor 96 (hence the symmetry sensor is shown in phantom in FIG. 3). For some applications, symmetry sensor 96 is distinct from, but can electronically interface with, control unit 94. For some applications in which control unit 94 comprises or interfaces with symmetry sensor 96, system 80 at least in part automatically performs the process of (1) inducing implants 82 to apply the excitatory current, (2) detecting a symmetry-related factor (e.g., a degree of symmetry), and (3) configuring implants 82 to increase the degree of symmetry. Control unit 94 is shown in FIG. 2 as a wand-type control unit (e.g., similar in appearance to that in the pacemaker art) purely as an illustrative example, and not by way of limitation.

For some applications, symmetry sensor 96 is distinct from control unit 94 and the operating physician fully-manually or partially-manually controls control unit 94 (e.g., via a user interface 98), at least in part responsively to information received from the symmetry sensor. Interface 98 may also be used for applications in which the physician visually observes the degree of symmetry (e.g., when no symmetry sensor is used). For some applications, symmetry sensor 96 comprises symmetry sensor 56, described hereinabove with reference to FIG. 2.

As described hereinabove, in contrast to system 40 described hereinabove with reference to FIG. 2, system 80 typically does not comprise an implantable control unit that is distinct from the neurostimulator implants. Thus, compared to system 40, instead of implantable control unit 44 being calibratable, at least one of implants 82 is calibratable.

Figure 4:
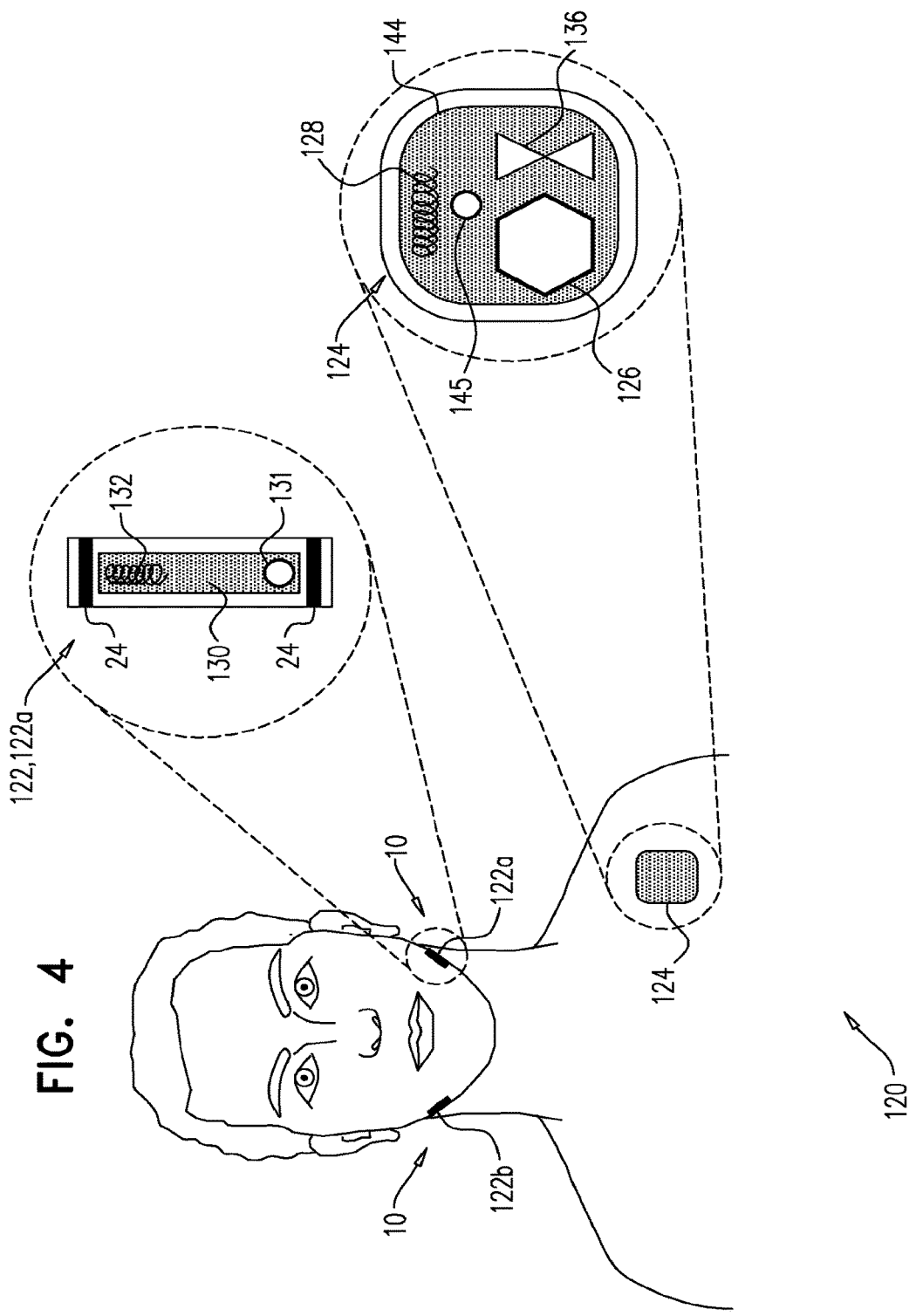

Reference is made to FIG. 4, which is a schematic illustration of a system 120, comprising two neurostimulator implants 122 (e.g., a first neurostimulator implant 122a and a second neurostimulator implant 122b), and an implantable (e.g., subcutaneously implantable) control unit 124 that comprises circuitry 144 comprising a breathing sensor 126 and a symmetry sensor 136, in accordance with some applications of the invention. Implantable control unit 124 (e.g., circuitry 144 thereof) typically comprises an antenna 128 and is configured to drive the antenna to transmit at least one wireless signal when breathing sensor 126 detects a sleep apnea event. Implants 122 are typically identical to implants 42 described hereinabove, mutatis mutandis.

Each implant 122 comprises one or more (e.g., two) electrodes 24, and circuitry 130 comprising an antenna 132. Circuitry 130 is configured to receive (e.g., via antenna 132) the wireless signal from control unit 124, and at least in part responsively to the wireless signal, to drive the electrodes 24 to apply the excitatory current to the hypoglossal nerve. For example, implant 122 (e.g., circuitry 130 thereof) may comprise a driver 131, configured to drive electrodes 24. Each implant 122 is independently addressable by control unit 124, e.g., by the wireless signal from the control unit being encoded. This allows control unit 124 to drive each implant to apply current that is different in one or more characteristics from current driven by the other implant, and thereby to control a balance between the currents of the implants, as described hereinbelow. Typically, control unit 124 drives both implants 122 at generally the same time (e.g., as described hereinabove, mutatis mutandis).

Typically, implants 122 are powered by control unit 124 via the wireless signal. That is, typically the wireless signal includes wireless power, and control unit 124 thus wirelessly drives circuitry 130 of implants 122 to drive electrodes 24 to apply the excitatory current. For example, antenna 132 may comprise an induction antenna (e.g., an induction loop) or a rectifying antenna, and control unit 124 (e.g., circuitry 144 thereof) may comprise a driver 145, configured to drive electrodes 24 via the wireless power.

Control unit 124 comprises a symmetry sensor 136 configured to detect a symmetry-related factor (e.g., degree of symmetry) of the subject. For some applications, symmetry sensor 136 comprises symmetry sensor 56, components, and/or functionality thereof. That is, compared to systems 40 and 80, symmetry-detecting functionality is moved from the extracorporeal control unit (54 or 94) to implantable control unit 124.

Subsequent to implantation of implants 122 and control unit 124 (e.g., immediately subsequently, or following a subsequent activation of the implants and/or the control unit), system 120 automatically calibrates itself. Control unit 124 drives implants 122 to apply the excitatory current, and symmetry sensor 136 detects a symmetry-related factor of the subject in response to the current, e.g., a degree of mechanical and/or electrical symmetry of contraction of the tongue. In response to the detected symmetry-related factor, control unit 124 (e.g., circuitry 144 thereof) configures (e.g., reconfigures) the wireless signal via which it drives implants 122 so as to calibrate the excitatory currents applied by the implants (e.g., by adjusting the excitatory current applied by at least one of the implants). For example, if the tongue of the subject moves toward one side during contraction, control unit 124 may increase the amplitude of the current of one of implants 122 and/or reduce the amplitude of the current applied by the other implant (e.g., as described hereinabove, mutatis mutandis). Typically, the process of calibrating the excitatory currents to increase symmetry is an iterative process, and further typically continues beyond an initial configuration period, e.g., continues for the life of system 120.

Because control unit 124 typically drives implants 122 to apply the excitatory current only when breathing sensor 126 detects a sleep apnea event, for some applications it is desirable to conduct an initial calibration step prior to reliance on system 120 to treat a true sleep apnea event: Subsequent to implantation of implants 122 and control unit 124, a physician initiates the initial calibration step by inducing (e.g., wirelessly) control unit 124 to drive the implants as though breathing sensor 126 had detected a sleep apnea event, such that the control unit (e.g., circuitry 144 thereof) may configure the wireless signal and thereby calibrate the excitatory currents. For some applications, the physician may conduct one or more additional (e.g., manual) configurations using an extracorporeal control unit, such as those described hereinabove, mutatis mutandis.

As described hereinabove, in contrast to systems 40 and 80 described hereinabove with reference to FIG. 2, system 120 typically does not comprise an extracorporeal control unit comprising or interfacing with a symmetry sensor. Thus, compared to systems 40 and 80, symmetry-detecting functionality and signal-configuring functionality is moved from the extracorporeal control unit to implantable control unit 124.

Figure 5:
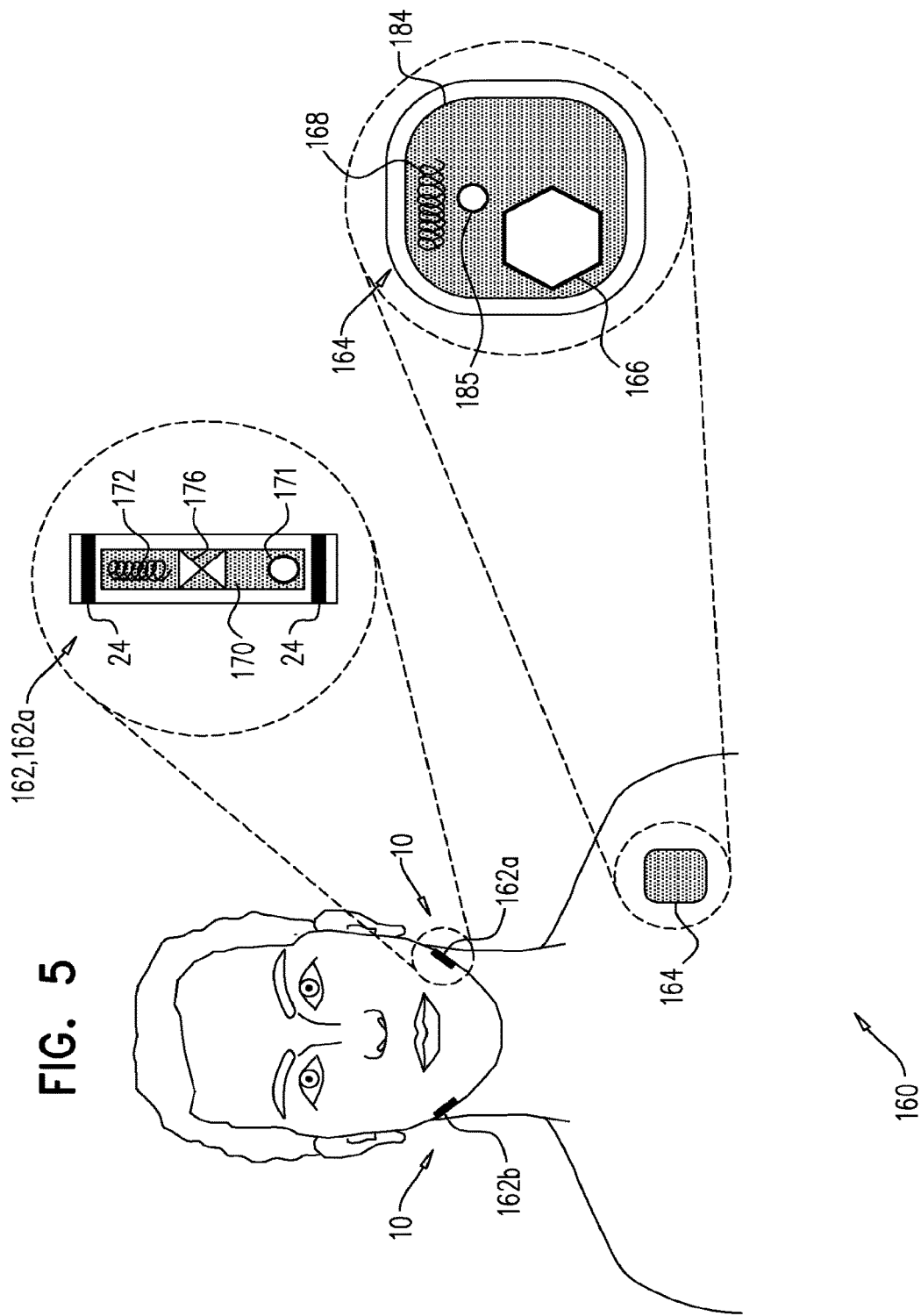
Figure 6:
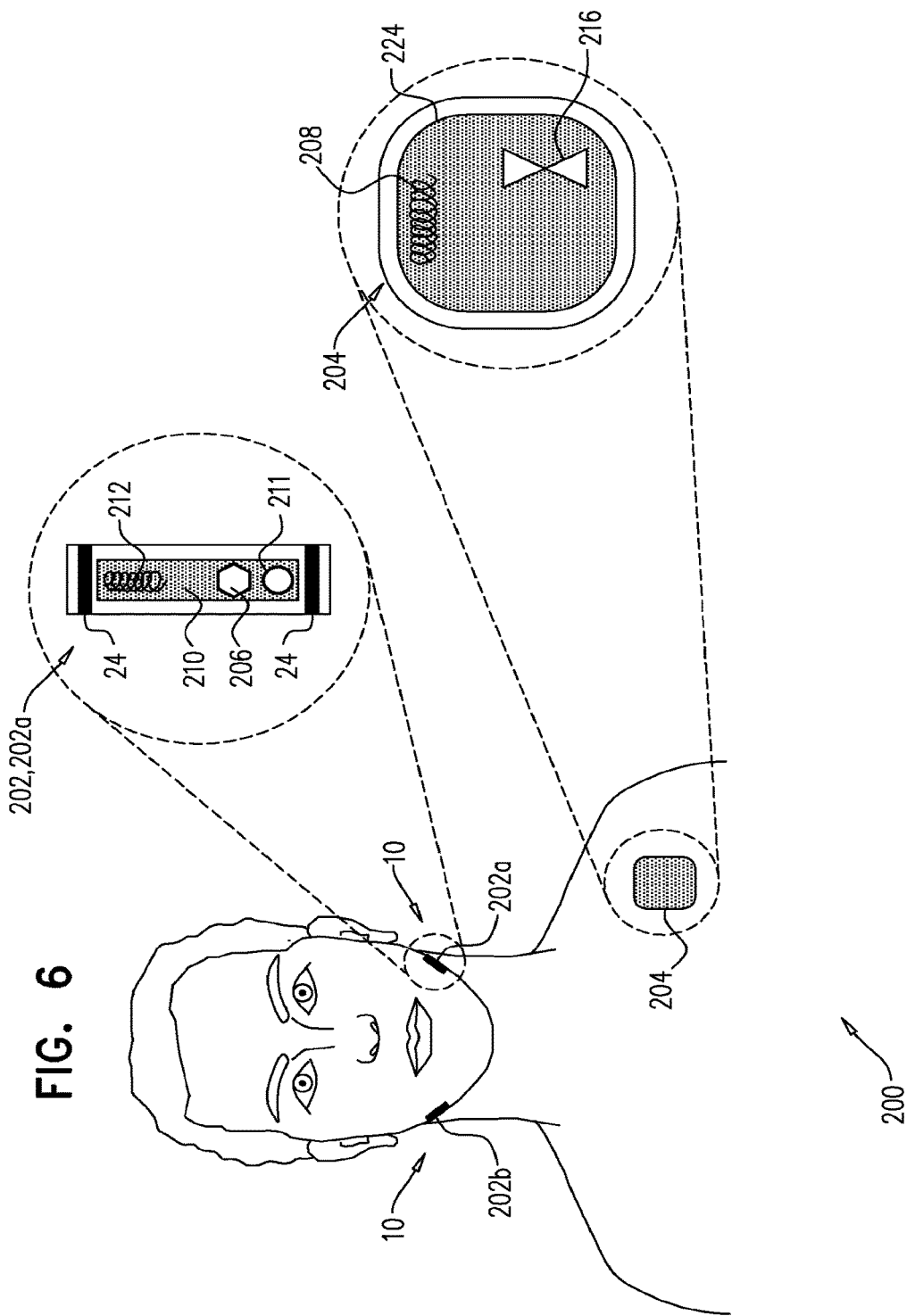

Reference is made to FIGS. 5 and 6, which are schematic illustrations of respective systems, each system comprising two neurostimulator implants and an implantable control unit, in accordance with some applications of the invention. FIG. 5 shows a system 160 comprising two neurostimulator implants 162 (e.g., a first neurostimulator implant 162a and a second neurostimulator implant 162b) and an implantable control unit 164, and FIG. 6 shows a system 200 comprising two neurostimulator implants 202 (e.g., a first neurostimulator implant 202a and a second neurostimulator implant 202b) and an implantable control unit 204. Systems 160 and 200 each comprise an implantable breathing sensor and an implantable symmetry sensor, and both have automatic-calibration functionality such as described hereinabove for system 120, mutatis mutandis. Typically, the automatic-calibration functionality of systems 160 and 200 is identical to that of system 120 except for differences described hereinbelow.

System 160 (FIG. 5) comprises a breathing sensor 166 that is a component of implantable control unit 164 (e.g., of circuitry 184 thereof), and a symmetry sensor 176 that is a component of at least one of implants 162 (e.g., of circuitry 170 thereof). That is, (1) control unit 164 comprises breathing sensor 166, in addition to an antenna 168, and (2) at least one of implants 162 comprises symmetry sensor 176, in addition to an antenna 172. Implantable control unit 164 detects (using breathing sensor 166) the breathing-related parameter, and responsively transmits a wireless signal (using antenna 168), as described hereinabove for implantable control unit 44, breathing sensor 46 and antenna 168 of system 40, mutatis mutandis, and/or as described for implantable control unit 124, breathing sensor 126, and antenna 128 of system 120, mutatis mutandis.

For some applications, implants 162 (e.g., circuitry 170 thereof) each comprise a driver 171, configured to drive electrodes 24. For some applications, implantable control unit 164 (e.g., circuitry 184 thereof) comprises a driver 185, configured to wirelessly drive electrodes 24 of both implants 162. System 160 automatically calibrates the excitatory currents of the implants 162 in response to symmetry sensor 176 (of one or both implants) detecting a symmetry-related factor of the subject.

In response to the detected symmetry-related factor, at least one of implants 162 configures circuitry 170 thereof so as to adjust at least one parameter of the excitatory current applied by that implant. For some applications, implants 162 are configured to wirelessly communicate via respective antennas 172 in order to collectively detect the symmetry-related factor, and/or to adjust the at least one parameter of the excitatory current applied by at least one of the implants.

System 200 (FIG. 6) comprises a symmetry sensor 216 that is a component of implantable control unit 204 (e.g., of circuitry 224 thereof), and a breathing sensor 206 that is a component of at least one of implants 202 (e.g., of circuitry 210 thereof). That is, (1) control unit 204 comprises symmetry sensor 216, in addition to an antenna 208, and (2) at least one of implants 202 comprises breathing sensor 206, in addition to an antenna 212. Implants 202 are configured to apply the excitatory current in response to breathing sensor 206 detecting the breathing-related parameter as described hereinabove for implants 82 and breathing sensor 86 of system 80, mutatis mutandis. Implants 202 (e.g., circuitry 210 thereof) typically each comprise a driver 211, configured to drive electrodes 24. System 200 automatically self-calibrates in response to the symmetry-related parameter, by implantable control unit 204 (e.g., circuitry 224 thereof) detecting the symmetry-related parameter using symmetry sensor 216, and responsively configuring one or more of implants 202 (e.g., circuitry 210 thereof), as described for some applications of extracorporeal control unit 94 and symmetry sensor 96, mutatis mutandis.

Figure 7:
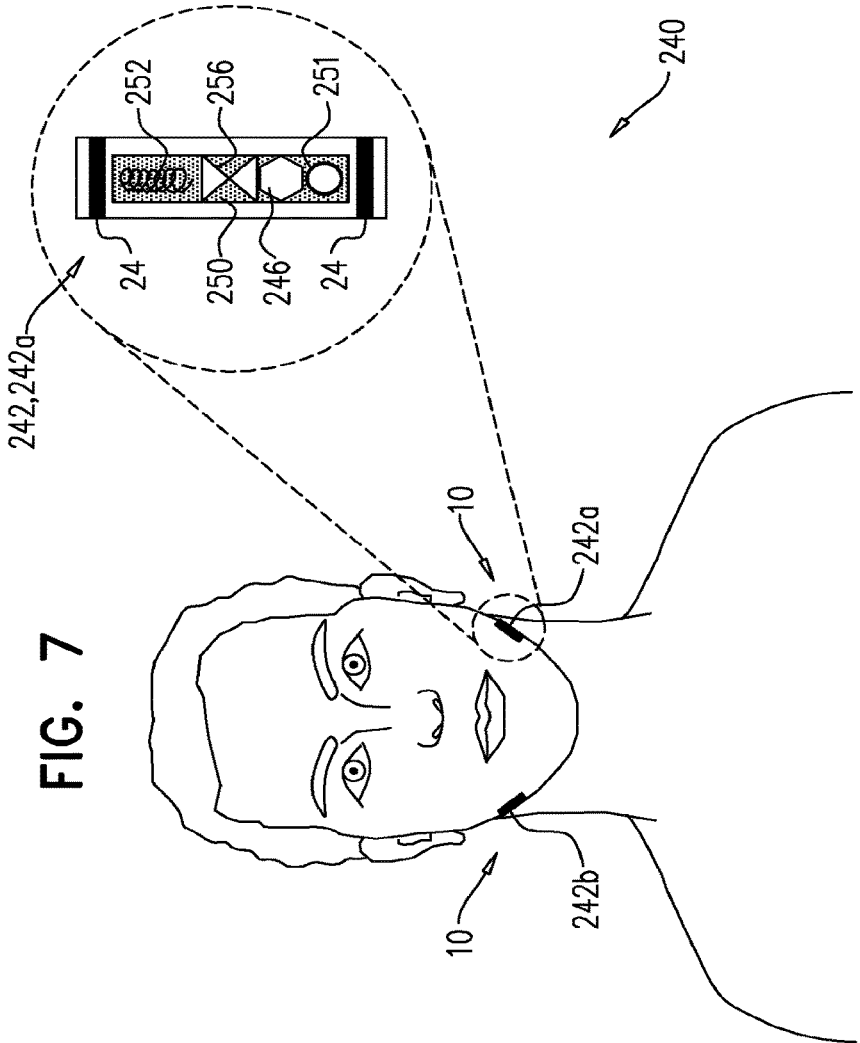

Reference is made to FIG. 7, which is a schematic illustration of a system 240 comprising two neurostimulator implants 242 (e.g., a first neurostimulator implant 242a and a second neurostimulator implant 242b), each implant comprising circuitry 250 and one or more electrodes 24, in accordance with some applications of the invention.

At least one of implants 242 (e.g., circuitry 250 thereof) comprises a breathing sensor 246 and at least one of implants 242 (e.g., circuitry 250 thereof) comprises a symmetry sensor 256. Breathing sensor 246 typically comprises breathing sensor 86 and/or breathing sensor 206, described hereinabove, and system 240 typically applies the excitatory current in response to the detected breathing-related parameter as described for systems 80 and/or 200, mutatis mutandis. Implants 242 (e.g., circuitry 250 thereof) typically each comprise a driver 251, configured to drive electrodes 24. Symmetry sensor 256 typically comprises symmetry sensor 176, described hereinabove, and system 240 typically calibrates the excitatory currents of the implants thereof (e.g., by configuring the circuitry of the implants) in response to the detected symmetry-related parameter as described for system 160, mutatis mutandis. System 240 (e.g., the functionality thereof) is typically entirely provided by implants 242, although a physician may optionally configure (e.g., manually configure) implants 242 via an antenna 252 of each implant.

For some applications of the invention, both implant 242a and implant 242b comprise a respective breathing sensor 246 and a respective symmetry sensor 256. For some applications of the invention, both implant 242a and implant 242b comprise a respective breathing sensor 246, but only one of the implants comprises symmetry sensor 256. For some applications of the invention, both implant 242a and implant 242b comprise a respective symmetry sensor 256, but only one of the implants comprises breathing sensor 246. For some applications of the invention, only one of implants 242 comprises breathing sensor 246, and only one of the implants comprises symmetry sensor 256.

Figure 8:
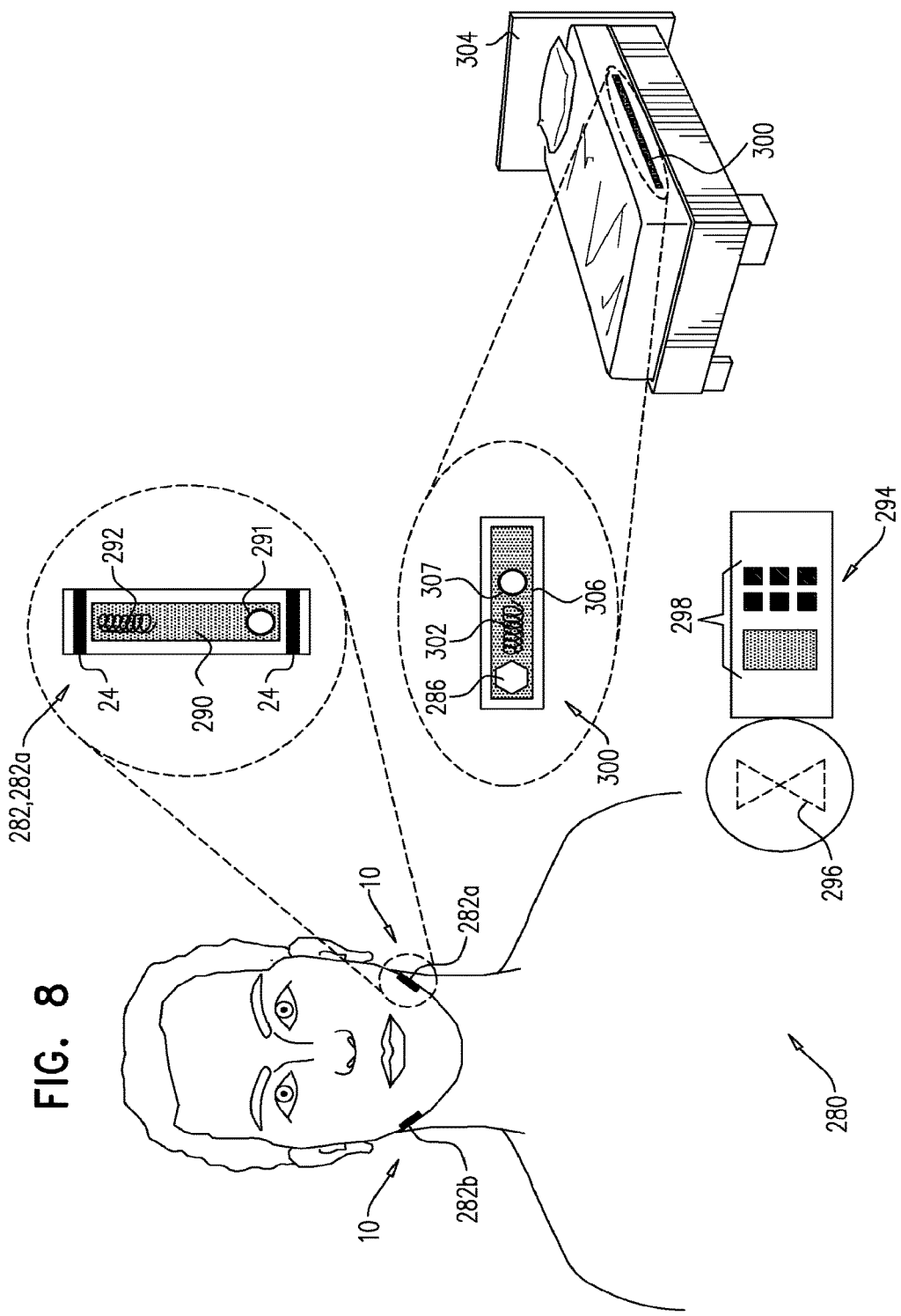

Reference is made to FIG. 8, which is a schematic illustration of a system 280, comprising two neurostimulator implants 282 (e.g., a first neurostimulator implant 282a and a second neurostimulator implant 282b), each implant comprising one or more electrodes 24 and circuitry 290 that comprises an antenna 292, in accordance with some applications of the invention. Implants 282 are configured to receive a wireless signal via antenna 292, and to responsively apply the excitatory current to the hypoglossal nerve of the subject, as described hereinabove for implants 42 and 122, mutatis mutandis. For some applications, implants 282 (e.g., circuitry 290 thereof) each comprise a driver 291, configured to drive electrodes 24.

System 280 further comprises a bedside extracorporeal control unit 300 comprising circuitry 306 that comprises an antenna 302 and a breathing sensor 286, configured to detect a breathing-related parameter of the subject. Control unit 300 is configured to be placed in the vicinity of a bed 304 of the subject, such as under a mattress or on a nightstand of the subject. In response to detecting the parameter (e.g., in response to detecting a sleep apnea event), control unit 300 transmits, via an antenna 302 thereof, the wireless signal to which implants 282 respond. In this manner, system 280 is thus similar to system 40, with the functionalities of breathing detection and wireless signal transmission performed by bedside control unit 300 rather than by implantable control unit 44. For some applications, control unit 300 (e.g., circuitry 306 thereof) comprises a driver 307, configured to wirelessly drive electrodes 24 of both implants 282.

System 280 further comprises an additional extracorporeal control unit 294, configured to configure system 280 so as to calibrate the excitatory current applied by implant 282a and that applied by implant 282b. For some applications, control unit 294 is configured to configure implants 282 (e.g., circuitry 290 thereof) to calibrate the excitatory currents, e.g., as described with reference to control unit 94 configuring implants 82 of system 80, mutatis mutandis. For example, control unit 294 typically comprises a user interface 298, and for some applications comprises and/or electronically interfaces with a symmetry sensor 296. For some applications, control unit 294 is configured to configure bedside control unit 300 (e.g., circuitry 306 thereof) to calibrate the excitatory currents, e.g., as described with reference to control unit 54 configuring implantable control unit 44 of system 40, mutatis mutandis.

Figure 9:
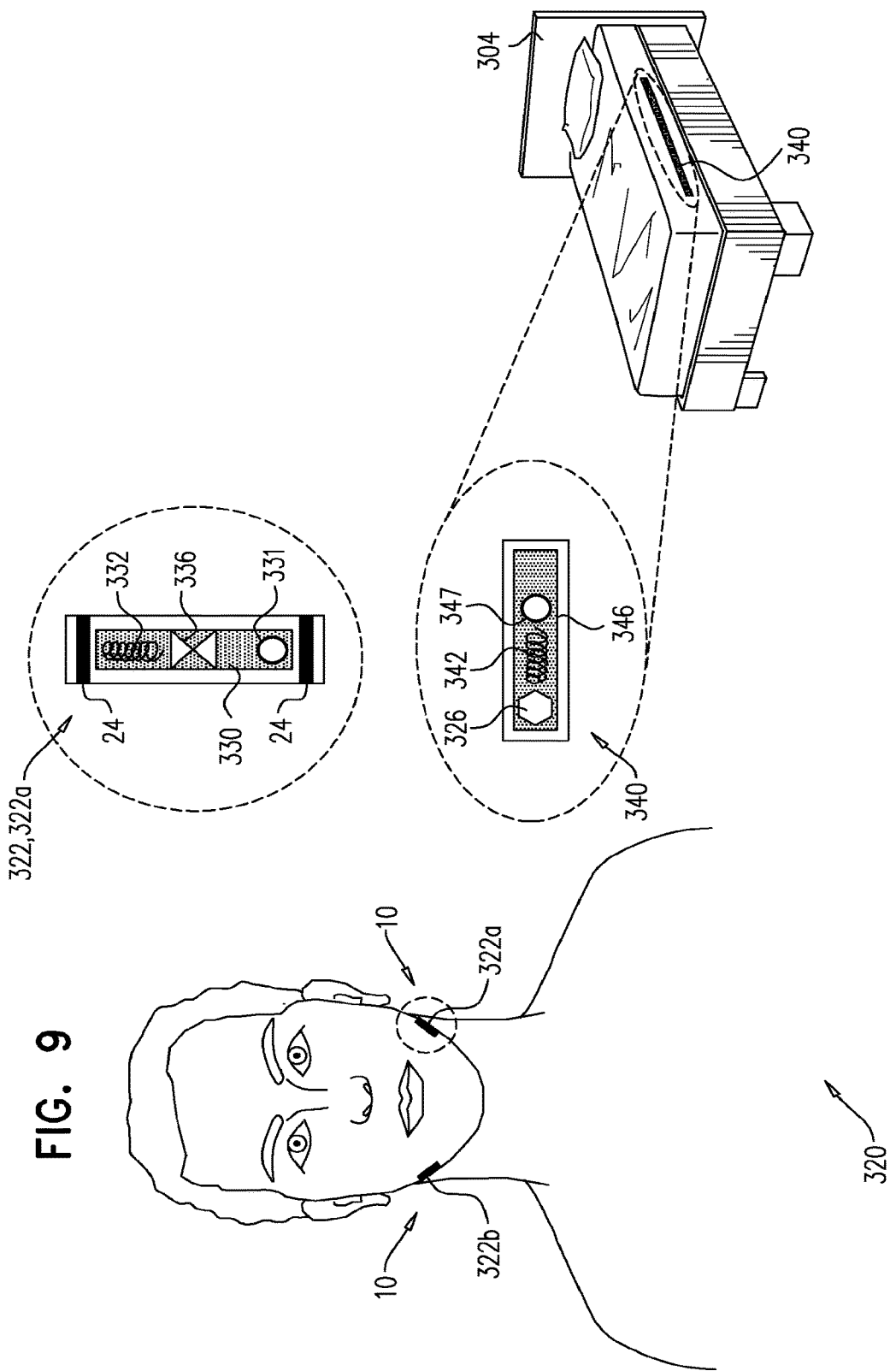

Reference is made to FIG. 9, which is a schematic illustration of a system 320, comprising two neurostimulator implants 322 (e.g., a first neurostimulator implant 322a and a second neurostimulator implant 322b), and a bedside extracorporeal control unit 340, in accordance with some applications of the invention. Bedside control unit 340 comprises circuitry 346 comprising an antenna 342 and a breathing sensor 326. Bedside control unit 340 and components thereof are typically identical to bedside control unit 300 and components thereof, described hereinabove. Each implant 322 comprises one or more electrodes 24 and circuitry 330 that comprises an antenna 332. At least one of implants 322 (e.g., circuitry 330 thereof) further comprises a symmetry sensor 336. Implants 322 typically detect a symmetry-related factor of the subject, and responsively configure circuitry 330 to calibrate the excitatory currents of the implants, as described hereinabove for implants 162, mutatis mutandis. For some applications of the invention, system 320 is thus similar to system 160, with the functionalities of breathing detection and wireless signal transmission performed by bedside control unit 340 rather than by implantable control unit 164. For some applications, implants 322 (e.g., circuitry 330 thereof) each comprise a driver 331, configured to drive electrodes 24. For some applications, control unit 340 (e.g., circuitry 346 thereof) comprises a driver 347, configured to wirelessly drive electrodes 24 of both implants 162.

Figure 10:
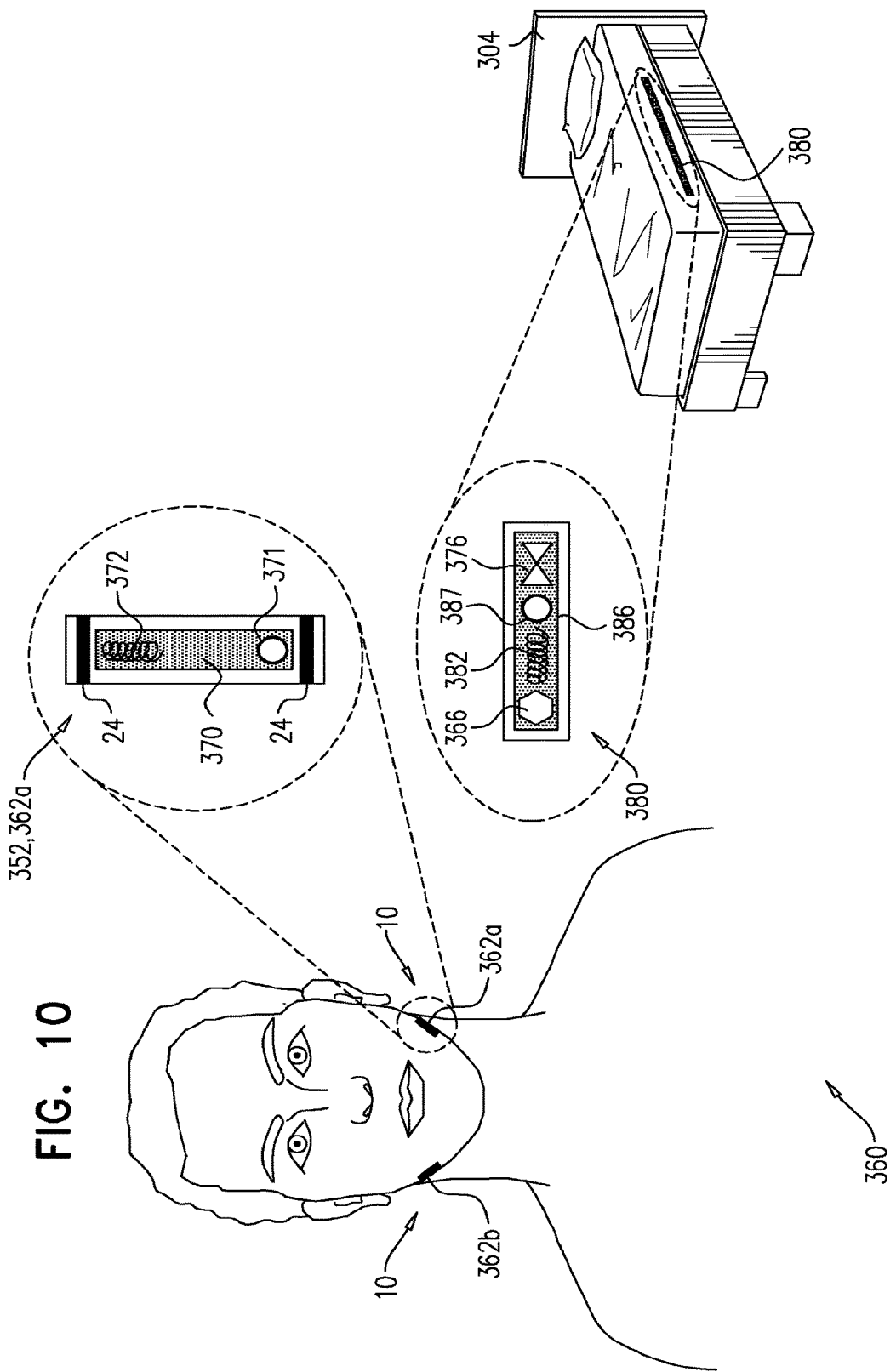

Reference is made to FIG. 10, which is a schematic illustration of a system 360, comprising two neurostimulator implants 362 (e.g., a first neurostimulator implant 362a and a second neurostimulator implant 362b), and a bedside extracorporeal control unit 380, in accordance with some applications of the invention. Implants 362 comprise circuitry 370 and are configured to receive a wireless signal via an antenna 372, and to responsively apply the excitatory current to the hypoglossal nerve of the subject, as described hereinabove for implants 42 and 122, mutatis mutandis. For example, implants 362 (e.g., circuitry 370 thereof) may comprise a driver 371, configured to drive electrodes 24.

Bedside control unit 380 comprises an antenna 382 and circuitry 386 comprising a breathing sensor 366 and a symmetry sensor 376. Breathing sensor 366 typically comprises breathing sensor 286 described hereinabove. For some applications, control unit 380 (e.g., circuitry 386 thereof) comprises a driver 387, configured to wirelessly drive electrodes 24 of both implants 362. Thus, bedside control unit 380 is similar to bedside control unit 300 and/or bedside control unit 340, with the addition of symmetry sensor 376. Thus system 380 is (1) similar to system 300, with the functionality of symmetry detection and calibration of excitatory currents performed by bedside control unit 380 rather than by implantable control unit 294, and/or (2) similar to system 340, with the functionality of symmetry detection and calibration of excitatory currents performed by bedside control unit 380 rather than by implants 322.

Figure 11:
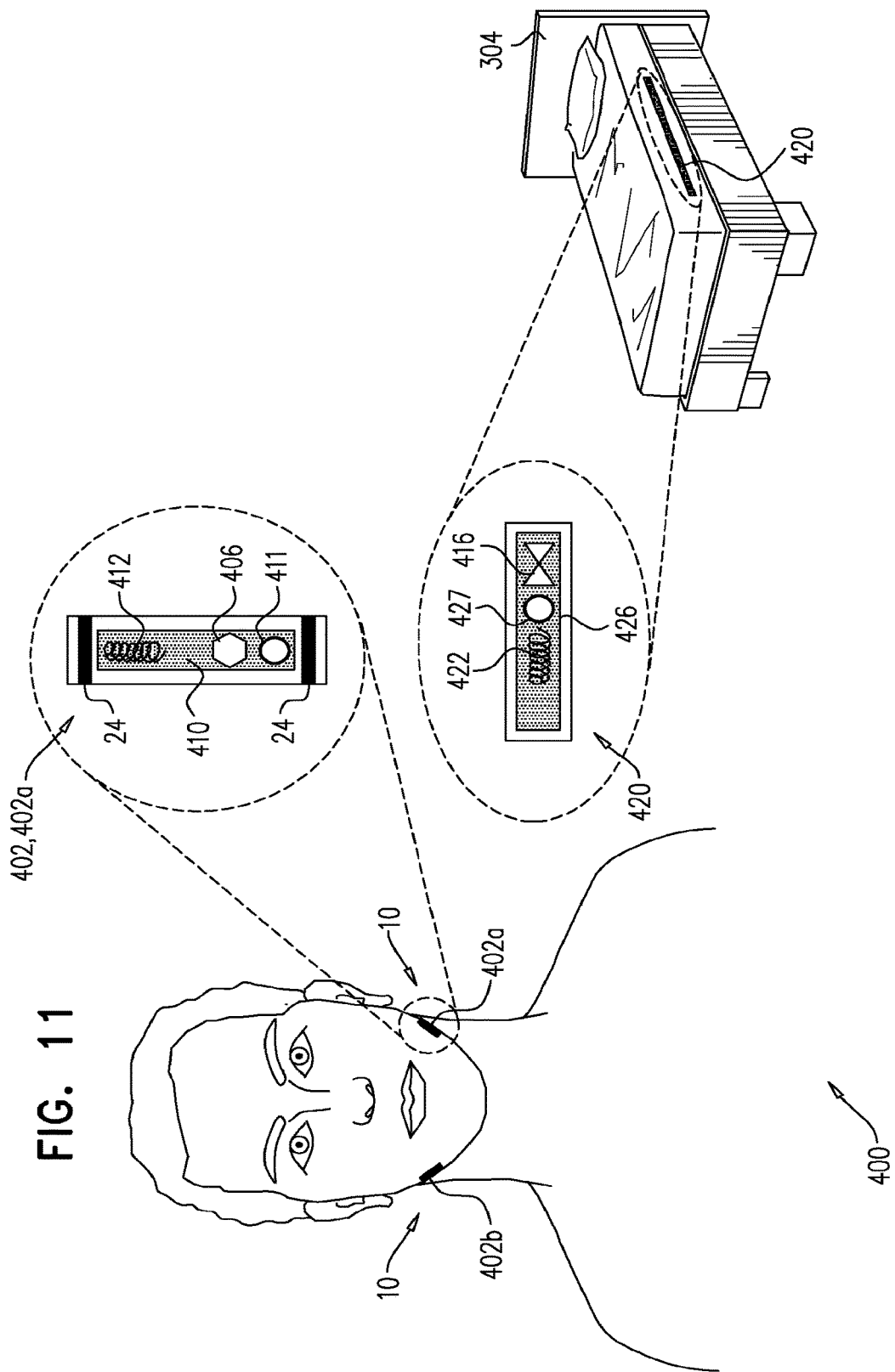

Reference is made to FIG. 11, which is a schematic illustration of a system 400, comprising two neurostimulator implants 402 (e.g., a first neurostimulator implant 402a and a second neurostimulator implant 402b), and a bedside extracorporeal control unit 420, in accordance with some applications of the invention. Control unit 420 comprises circuitry 426 that comprises a symmetry sensor 416 and an antenna 412. At least one of implants 402 (e.g., circuitry 410 thereof) comprises a breathing sensor 406. For some applications, implants 402 (e.g., circuitry 410 thereof) each comprise a driver 411, configured to drive electrodes 24. For some applications, control unit 420 (e.g., circuitry 426 thereof) comprises a driver 427, configured to wirelessly drive electrodes 24 of both implants 402. System 400 is thus (1) similar to system 360, with the functionality of breathing detection performed by at least one of implants 402 rather than by bedside control unit 380, and (2) similar to system 200, with the functionalities of symmetry detection and calibration of excitatory currents performed by control unit 420 rather than by implantable control unit 204.

Figure 12:
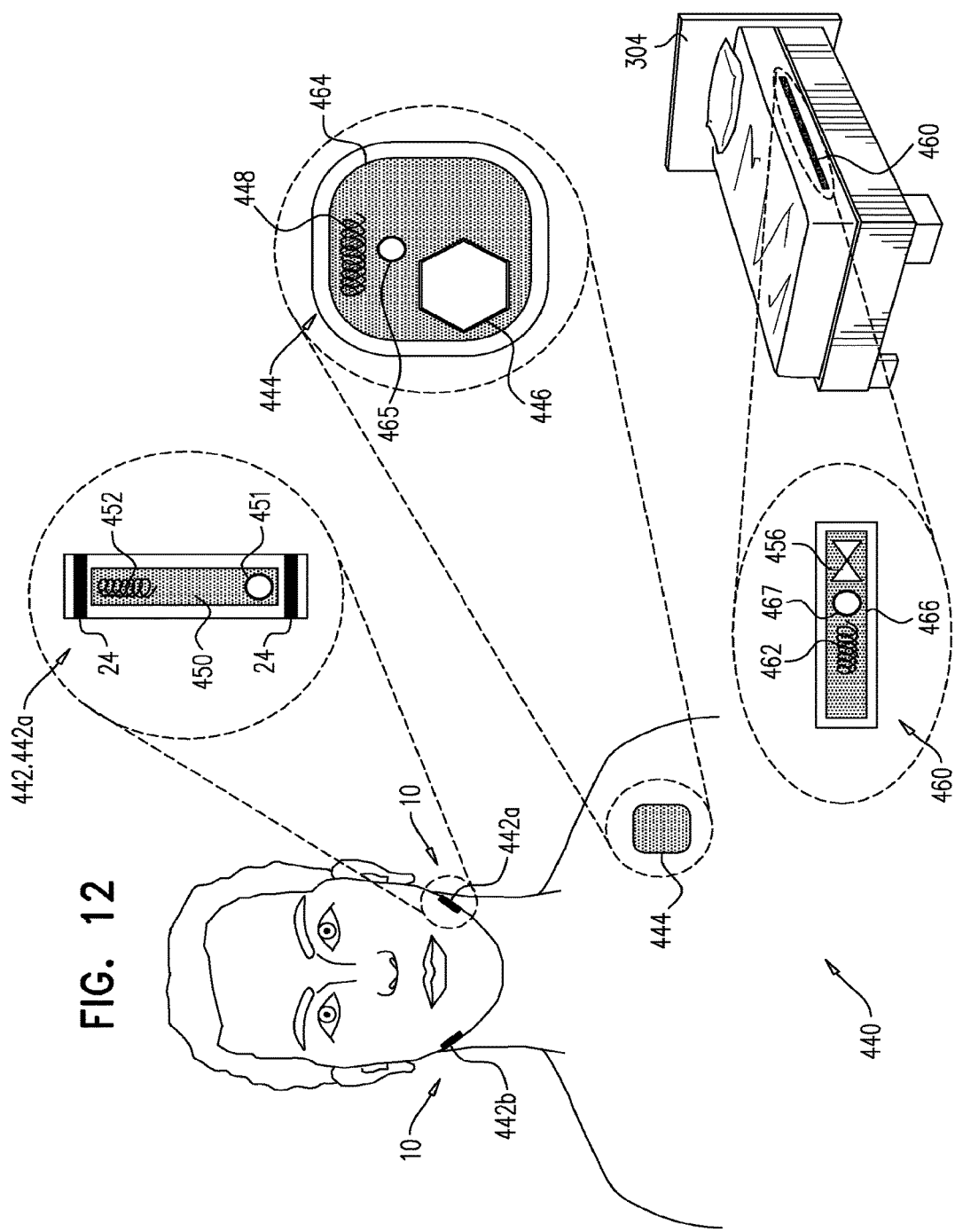
Figure 13:
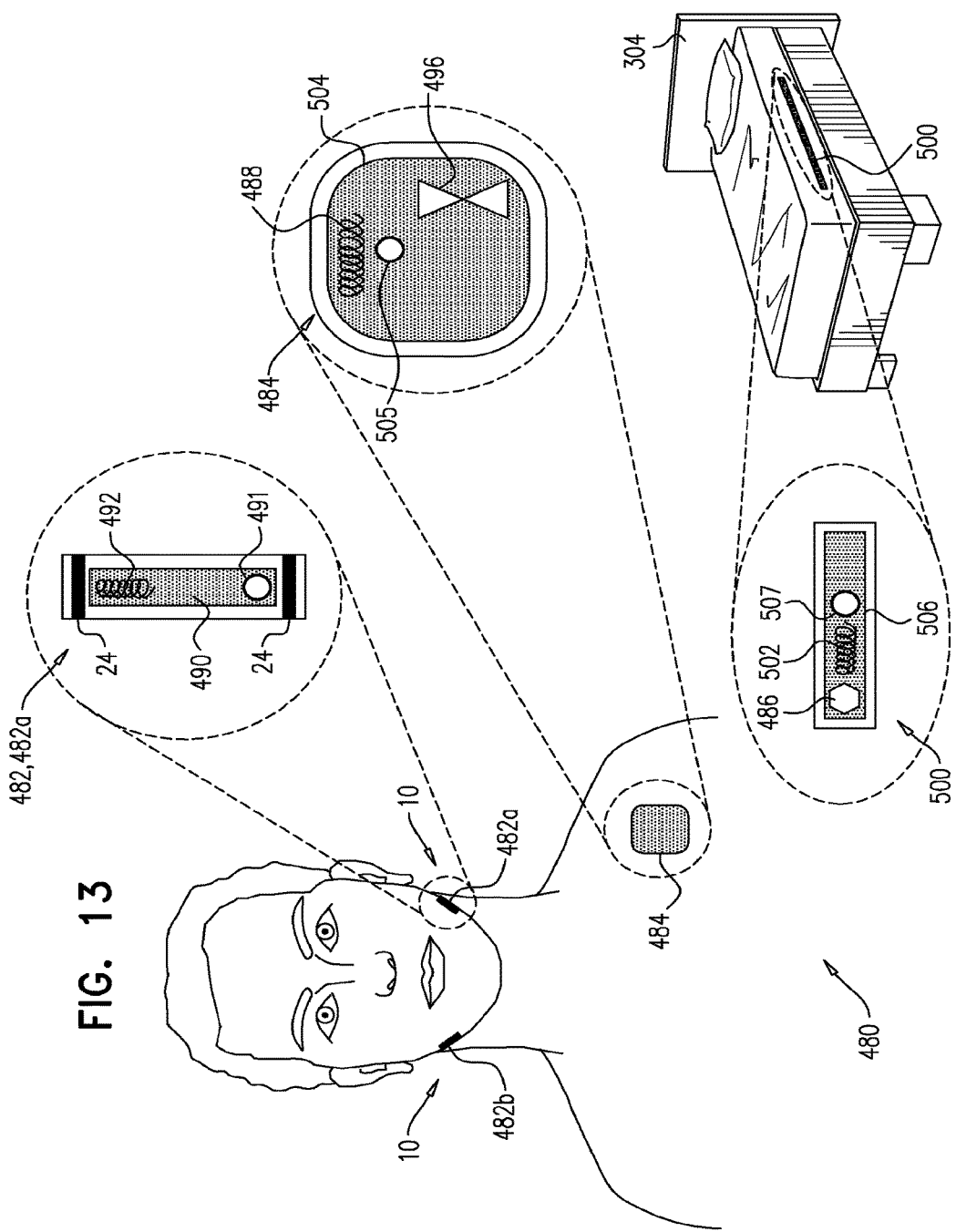

Reference is made to FIGS. 12-13, which are schematic illustrations of systems, each system comprising two neurostimulator implants, an implantable control unit and a bedside control unit, in accordance with some applications of the invention. It will be appreciated from the descriptions hereinabove that it is possible to assign breathing sensing and symmetry sensing to various elements of apparatus, both implantable and extracorporeal, with a similar result of calibration of the excitatory currents that are applied in response to the breathing-related factor. Two further arrangements are now described with reference to FIGS. 12-13.

FIG. 12 shows a system 440 in which symmetry sensing is performed by a symmetry sensor 456 of circuitry 466 of a bedside control unit 460 that, in response to detection of the symmetry-related factor, wirelessly configures (e.g., via an antenna 462) an implantable control unit 444 (e.g., circuitry 464 thereof). Control unit 444 comprises a breathing sensor 446, and transmits, via an antenna 448, a wireless signal that is received by an antenna 452 of circuitry 450 of two neurostimulator implants 442 (e.g., a first neurostimulator implant 442a and a second neurostimulator implant 442b) that responsively apply the excitatory current. The configuration of control unit 444 by control unit 460 configures the excitatory currents of the two implants, e.g., as described for implantable control unit 44, mutatis mutandis. Alternatively, control unit 460 calibrates the excitatory currents by directly configuring implants 442 (e.g., circuitry 450 thereof).

For some applications, implants 442 (e.g., circuitry 450 thereof) each comprise a driver 451, configured to drive electrodes 24. For some applications, control unit 444 (e.g., circuitry 464 thereof) comprises a driver 465, configured to wirelessly drive electrodes 24 of both implants 442. For some applications, control unit 460 (e.g., circuitry 466 thereof) comprises a driver 467, configured to wirelessly drive electrodes 24 of both implants 442.

FIG. 13 shows a system 480 in which breathing sensing is performed by a breathing sensor 486 of circuitry 506 of a bedside control unit 500. In response to detection of the breathing-related factor, control unit 500 transmits, via an antenna 502, a wireless signal that is received by a respective antenna 492 of circuitry 490 of two neurostimulator implants 482 (e.g., a first neurostimulator implant 482a and a second neurostimulator implant 482b) that responsively apply the excitatory current. An implantable control unit 484 comprises circuitry 504 comprising a symmetry sensor 496 that detects the symmetry-related factor, and responsively configures (e.g., via an antenna 502) neurostimulator implants 482 (e.g., circuitry 490 thereof) so as to calibrate the excitatory currents of the two implants (e.g., as described for implantable control unit 204, mutatis mutandis). Alternatively, control unit 484 receives the wireless signal from control unit 500 and responsively transmits a second wireless signal that drives implants 482. For such applications, implantable control unit 484 calibrates the excitatory currents by configuring the second wireless signal (e.g., by configuring circuitry 504 of the implantable control unit).

For some applications, implants 482 (e.g., circuitry 490 thereof) each comprise a driver 491, configured to drive electrodes 24. For some applications, control unit 484 (e.g., circuitry 504 thereof) comprises a driver 505, configured to wirelessly drive electrodes 24 of both implants 482. For some applications, control unit 500 (e.g., circuitry 506 thereof) comprises a driver 507, configured to wirelessly drive electrodes 24 of both implants 482.

Reference is again made to FIGS. 1-13. For some applications, the implants described herein are configured to become fixed with respect to the anatomy of the subject after implantation. For example, the implants may comprise hooks or barbs that penetrate into tissue, and/or may be surface treated or coated with a material that promotes tissue growth and/or fibrosis (e.g., expanded polytetrafluoroethylene).

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use with a body of a subject, the method comprising:
   detecting a breathing-related factor of the subject;
   in response to the detected breathing-related factor:
      applying a first electrical current to a first hypoglossal nerve of the subject, and
      applying a second electrical current to a second hypoglossal nerve of the subject;
   detecting a symmetry of a response of the subject to the applied first and second currents; and
   in response to the detected symmetry, configuring at least one current selected from the group consisting of: the first current and the second current.

2. The method according to claim 1, wherein detecting the breathing-related factor comprises extracorporeally detecting the breathing-related factor.

3. The method according to claim 1, wherein:
   detecting the breathing-related parameter comprises detecting the breathing-related parameter using a breathing sensor;
   applying the first electrical current comprises applying the first electrical current using a first electrode disposed in a vicinity of the first hypoglossal nerve;

applying the second electrical current comprises applying the second electrical current using a second electrode disposed in a vicinity of the second hypoglossal nerve; and configuring the at least one selected current comprises configuring the at least one selected current using circuitry configured to configure the at least one selected current in response to the detected symmetry.

4. The method according to claim 3, wherein detecting the symmetry comprises detecting the symmetry using a symmetry sensor.

5. The method according to claim 4, wherein detecting the symmetry comprises detecting a mechanical symmetry of the response of the subject.

6. The method according to claim 4, wherein detecting the symmetry comprises detecting the symmetry using a symmetry sensor that includes an accelerometer.

7. The method according to claim 4, wherein detecting the symmetry comprises detecting an electrical symmetry of the response of the subject.

8. The method according to claim 4, wherein detecting the symmetry comprises detecting the symmetry using a symmetry sensor that includes an electrode.

9. The method according to claim 8, wherein detecting the symmetry comprises detecting the symmetry using a symmetry sensor that includes an electromyographic electrode.

10. The method according to claim 4, wherein:
detecting the symmetry comprises detecting the symmetry-related factor using an extracorporeal control unit that includes the symmetry sensor, and
the method further includes transmitting a wireless signal at least in part responsively to the detected symmetry.

11. The method according to claim 3, wherein:
the circuitry includes a first circuitry,
a first implant includes the first circuitry and the first electrode,
applying the first current comprises applying the first current using the first electrode of the first implant,
a second implant includes the second electrode and second circuitry, and
applying the second current comprises applying the second current using the second electrode of the second implant.

12. The method according to claim 11, wherein detecting the symmetry comprises detecting the symmetry using a symmetry sensor of a control unit, and wherein the method further comprises, using the control unit;
transmitting a wireless signal at least in part responsively to the detected symmetry, and
configuring the wireless signal to independently address the first implant and the second implant.

13. The method according to claim 11, wherein at least one implant selected from the group consisting of: the first implant and the second implant, includes the breathing sensor, and detecting the breathing-related factor comprises detecting the breathing-related factor using the breathing sensor of the at least one selected implant.

14. The method according to claim 11, wherein at least one implant selected from the group consisting of: the first implant and the second implant, includes a symmetry sensor, and detecting the symmetry comprises detecting the symmetry using the symmetry sensor of the at least one selected implant.

15. The method according to claim 3, wherein the circuitry includes circuitry of a control unit, and configuring the at least one selected current comprises configuring the at least one selected current using the circuitry of the control unit.

16. The method according to claim 15, wherein configuring the at least one selected current comprises configuring the at least one selected current using circuitry of an implantable control unit, disposed within the body of the subject.

17. The method according to claim 15, wherein the control unit includes the breathing sensor, and detecting the breathing-related factor comprises detecting the breathing-related factor using the breathing sensor of the control unit.

18. The method according to claim 15, wherein the control unit comprises a symmetry sensor, and wherein detecting the symmetry comprises detecting the symmetry using the symmetry sensor of the control unit.

19. The method according to claim 18, further comprising transmitting a wireless signal using the control unit, in response to detecting the symmetry.

20. A method, comprising:
implanting, in a vicinity of a first anatomical site of a subject, a first implant including at least one electrode and circuitry configured to drive the at least one electrode of the first implant to apply a first electrical current to the first anatomical site;
implanting, in a vicinity of a second anatomical site of a subject, a second implant including at least one electrode and circuitry configured to drive the at least one electrode of the second implant to apply a second electrical current to the second anatomical site; and
subsequently, detecting a symmetry of a response of the subject to the applied first and second currents, and in response to the detected symmetry, configuring at least one implant selected from the group consisting of: the first implant and the second implant.

21. The method according to claim 20, wherein implanting the first implant comprises implanting the first implant in a vicinity of a first hypoglossal nerve of the subject, and implanting the second implant comprises implanting the second implant in a vicinity of a second hypoglossal nerve of the subject.

22. The method according to claim 20, wherein detecting comprises detecting a mechanical symmetry of the response of the subject.

23. The method according to claim 20, wherein detecting comprises detecting an electrical symmetry of the response of the subject.

24. The method according to claim 20, wherein configuring comprises modifying the current applied by the at least one selected implant.

25. The method according to claim 24, wherein modifying comprises altering a balance of amplitude between the first electrical current and the second electrical current.

* * * * *